(12) United States Patent
Eisner et al.

(10) Patent No.: US 12,357,615 B2
(45) Date of Patent: Jul. 15, 2025

(54) COMPOSITIONS FOR THE TREATMENT OF BRAIN TUMORS

(71) Applicants: Kembi Therapeutics Pty Ltd, Carlton (AU); The Regents of the University of Michigan, Ann Arbor, MI (US); The United States Government as represented by The Department of Veterans Affairs, Washington, DC (US)

(72) Inventors: Joel Eisner, Chapel Hill, NC (US); Daniel Wahl, Ann Arbor, MI (US); Corey Speers, Ann Arbor, MI (US)

(73) Assignees: Kembi Therapeutics Pty Ltd, Carlton (AU); The Regents of the University of Michigan, Ann Arbor, MI (US); The United States Government as represented by The Department of Veterans Affairs, Washington, DC (US)

( * ) Notice: Subject to any disclaimer, the term of this patent is extended or adjusted under 35 U.S.C. 154(b) by 587 days.

(21) Appl. No.: 17/284,200

(22) PCT Filed: Oct. 11, 2019

(86) PCT No.: PCT/US2019/055818
§ 371 (c)(1),
(2) Date: Apr. 9, 2021

(87) PCT Pub. No.: WO2020/077197
PCT Pub. Date: Apr. 16, 2020

(65) Prior Publication Data
US 2022/0370415 A1 Nov. 24, 2022

Related U.S. Application Data

(60) Provisional application No. 62/744,342, filed on Oct. 11, 2018.

(51) Int. Cl.
*A61K 31/4192* (2006.01)
*A61K 31/4375* (2006.01)
(Continued)

(52) U.S. Cl.
CPC ...... *A61K 31/4192* (2013.01); *A61K 31/4375* (2013.01); *A61K 31/573* (2013.01); *A61P 35/00* (2018.01)

(58) Field of Classification Search
CPC ............ A61K 31/4192; A61K 31/4375; A61K 31/573; A61K 45/06; A61P 35/00; C07D 249/04
See application file for complete search history.

(56) References Cited

U.S. PATENT DOCUMENTS

2015/0209361 A1* 7/2015 Shih ........................ A61K 45/06
514/393
2016/0151394 A1* 6/2016 Auerbach ............ A61K 31/573
514/170

(Continued)

FOREIGN PATENT DOCUMENTS

WO WO 2017/117393 A1 7/2017

OTHER PUBLICATIONS

Chowdhury EA, et al. Understanding the brain uptake and permeability of small molecules through the BBB: A technical overview. J Cereb Blood Flow Metab. Aug. 2021;41(8):1797-1820. doi: 10.1177/0271678X20985946. Epub Jan. 14, 2021. PMID: 33444097; PMCID: PMC8327119. (Year: 2021).*

(Continued)

*Primary Examiner* — Bruck Kifle
*Assistant Examiner* — Kevin S Martin
(74) *Attorney, Agent, or Firm* — Wolf, Greenfield & Sacks, P.C.

(57) ABSTRACT

The instant invention describes pharmaceutical compositions and dosing regimens comprising radiation therapy and (Continued)

seviteronel with or without dexamethasone, and methods of treating diseases, disorders or symptoms thereof.

20 Claims, 6 Drawing Sheets

(51) Int. Cl.
*A61K 31/573* (2006.01)
*A61K 35/00* (2006.01)
*A61P 35/00* (2006.01)
*A61K 45/06* (2006.01)
*C07D 249/04* (2006.01)

(56) References Cited

U.S. PATENT DOCUMENTS

2018/0221364 A1\* 8/2018 Hoekstra ............... A61P 31/04
2021/0154209 A1 5/2021 Baskin-Bey et al.

OTHER PUBLICATIONS

Zalcman N, Canello T, Ovadia H, Charbit H, Zelikovitch B, Mordechai A, Fellig Y, Rabani S, Shahar T, Lossos A, Lavon I. Androgen receptor: a potential therapeutic target for glioblastoma. Oncotarget. Apr. 13, 2018;9(28): 19980-19993. doi: 10.18632/oncotarget.25007. PMID: 29731997; PMCID: PMC5929440. (Year: 2018).*

Sita TL, Petras KG, Wafford QE, Berendsen MA, Kruser TJ. Radiotherapy for cranial and brain metastases from prostate cancer: a systematic review. J Neurooncol. Jul. 2017; 133(3):531-538. doi: 10.1007/s11060-017-2460-6. Epub May 25, 2017. PMID: 28547593. (Year: 2017).*

Steeg PS, Camphausen KA, Smith QR. Brain metastases as preventive and therapeutic targets. Nat Rev Cancer. May 2011;11(5): 352-63. doi: 10.1038/nrc3053. Epub Apr. 7, 2011. PMID: 21472002; PMCID: PMC7351203. (Year: 2011).*

National Cancer Institute, Dexamethasone, 2015 (Year: 2015).*

International Search Report and Written Opinion for PCT/US2019/055818 mailed Jan. 30, 2020.

Invitation to Pay Additional Fees for PCT/US2019/055818 mailed Nov. 27, 2019.

International Preliminary Report on Patentability for PCT/US2019/055818 mailed Apr. 22, 2021.

Lorente et al., Tumour responses following a steroid switch from prednisone to dexamethasone in castration-resistant prostate cancer patients progressing on abiraterone. Br J Cancer. Dec. 9, 2014;111(12):2248-53. doi: 10.1038/bjc.2014.531. Epub Oct. 14, 2014.

Sun et al., Exth-15. Targeting Androgen Signaling In Glioblastoma (GBM) Using Seviteronel (Sevi), A Cyp17 Lyase And Androgen Receptor (AR) Inhibitor, Alone And In Combination With Radiation (RT). Neuro-Oncology. Nov. 2018;20(6):vi88.doi.org/10.1093/neuonc/noy148.364. 1 page.

Werner et al., Abstract 6267: Repurposing Antiandrogens To Overcome Therapy Resistance In Androgen Receptor-Positive Glioblastoma. In: Proceedings of the Annual Meeting of the American Association for Cancer Research 2020. Apr. 27-28, 2020. and Jun. 22-24;80(16): Abstract No. 6267. 2 pages.

Stein et al., Androgen synthesis inhibitors in the treatment of castration-resistant prostate cancer. Asian J Androl. May-Jun. 2014;16(3):387-400. doi: 10.4103/1008-682X.129133.

San Juan et al., 2022 Targeting Phenotypic Plasticity Prevents Metastasis And The Development Of Chemotherapy-Resistant Disease. MedRxiv doi: 10.1101/2022.03.21.22269988, https://www.medrxiv.org/content/10.1101/2022.03.21.22269988v1, 39 pages.

\* cited by examiner

Enhancement Ratio: 1.5 ± 0.1 (n=3)

Enhancement Ratio: 1.0 ± 0.1 (n=6)

Enhancement Ratio: 1.32 ± 0.05 (n=3)

Enhancement Ratio: 1.03 ± 0.02 (n=2)

COMPOSITIONS FOR THE TREATMENT OF BRAIN TUMORS

CROSS-REFERENCE TO RELATED APPLICATIONS

This Application is a National Phase Application under 35 U.S.C. 371 of PCT International Application No. PCT/US2019/055818, filed Oct. 11, 2019, which claims the benefit under 35 U.S.C. § 119(e) of the filing date of U.S. Provisional Application Serial No. 62/744,342, filed Oct. 11, 2018, the entire contents of which is incorporated by reference herein.

BACKGROUND

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the antifungal agent, commonly used to treat prostate cancer, ketoconazole contains a 1-imidazole group that binds to the heme iron present in the active site of the target enzyme CYP17 (17-α-hydroxylase, 17, 20-lyase) and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the commonly used prostate anticancer agent ketoconazole. It is believed that this off-target inhibition is caused primarily by the indiscriminate binding of the currently utilized 1-imidazole to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders, and symptoms thereof.

BRIEF SUMMARY OF THE INVENTION

The invention is directed towards compounds (e.g., any of those delineated herein), and methods of treating diseases, disorders, or symptoms thereof. The methods can comprise the compounds herein.

In one aspect, the invention provides a method of treating a subject suffering from or susceptible to a brain tumor, the method comprising the administration of radiation therapy and an effective amount of: 1) a compound of Formula (I), or pharmaceutically acceptable salt thereof; or 2) a pharmaceutical composition comprising a compound of Formula (I), or a pharmaceutically acceptable salt thereof, and a pharmaceutically acceptable carrier:

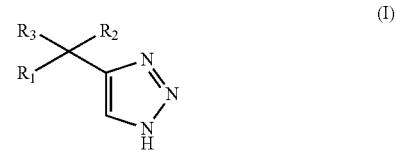

(I)

each $R_1$ and $R_2$ is independently optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl; and $R_3$ is H, OH, alkoxy, amino, alkylamino, or dialkylamino.

In another aspect, the compound of Formula (I), or pharmaceutically acceptable salt thereof; or pharmaceutical composition thereof, and radiation therapy are administered concurrently. In another aspect, the compound of Formula (I), or pharmaceutically acceptable salt thereof; or pharmaceutical composition thereof, and radiation therapy are administered sequentially.

In one aspect, the invention provides a method of treating a subject suffering from or susceptible to a brain tumor, the method comprising the administration of radiation therapy and an effective amount of a compound of Formula (I), or pharmaceutically acceptable salt thereof:

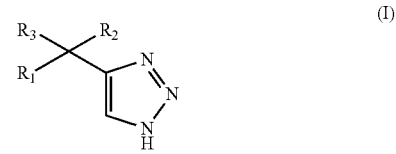

(I)

each $R_1$ and $R_2$ is independently optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl; and R₃ is H, OH, alkoxy, amino, alkylamino, or dialkylamino. In another aspect, the compound of Formula (I), or pharmaceutically acceptable salt thereof, and radiation therapy are administered concurrently. In another aspect, the compound of Formula (I), or pharmaceutically acceptable salt thereof, and radiation therapy are administered sequentially.

In one aspect, the invention provides a method of treating a subject suffering from or susceptible to a brain tumor, the method comprising the administration of radiation therapy and an effective amount of a pharmaceutical composition comprising: (1) a compound of Formula (I), or a pharmaceutically acceptable salt thereof, and (2) a pharmaceutically acceptable carrier:

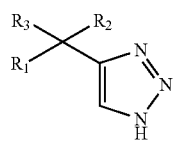
(I)

each R₁ and R₂ is independently optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl; and R₃ is H, OH, alkoxy, amino, alkylamino, or dialkylamino. In another aspect, the pharmaceutical composition comprising the compound of Formula (I), or pharmaceutically acceptable salt thereof, and radiation therapy are administered concurrently. In another aspect, the pharmaceutical composition comprising the compound of Formula (I), or pharmaceutically acceptable salt thereof, and radiation therapy are administered sequentially.

In another aspect, R₃ is OH.

In another aspect, R₂ is optionally substituted alkyl and R₃ is OH.

In another aspect, R₁ is optionally substituted aryl, R₂ is alkyl, and R₃ is OH.

In another aspect, R₁ is substituted aryl, R₂ is alkyl, and R₃ is OH.

In another aspect, R₁ is optionally substituted naphthyl, R₂ is alkyl, and R₃ is OH.

In another aspect, R₁ is substituted naphthyl, R₂ is alkyl, and R₃ is OH.

In another aspect, R₁ is naphthyl substituted with 1, 2, 3 or 4 substituents, independently selected from alkyl, alkoxy, haloalkoxy, cyano, halo, amino, mono-alkylamino, di-alkylamino, or heteroaryl.

In another aspect, R₁ is naphthyl substituted with 1, 2, 3 or 4 substituents, independently selected from alkyl, alkoxy, haloalkoxy, cyano, halo, amino, mono-alkylamino, di-alkylamino, or heteroaryl, R₂ is alkyl, and R₃ is OH.

In another aspect, the compound of Formula (I) is of Formula (II), or a pharmaceutically acceptable salt thereof:

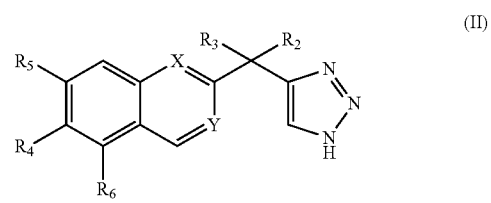
(II)

wherein X is CH or N; Y is CH or N; and R₄, R₅ and R₆ are each independently H, halogen, alkoxy, alkylthio, cycloalkoxy, fluoroalkoxy containing 1-5 fluorines, fluoroalkyl containing 1-5 fluorines, cyano, carboxamido, optionally substituted aryl, or optionally substituted heteroaryl. In another aspect, X is CH. In another aspect, X is N. In another aspect, Y is CH. In another aspect, Y is N. In another aspect, X and Y are each CH. In another aspect, X is NH and Y is CH. In another aspect, R₂ is optionally substituted alkyl. In another aspect, R₂ is alkyl. In another aspect, R₂ is isopropyl. In another aspect, R₃ is OH. In another aspect, X and Y are each CH; and R₂ is optionally substituted alkyl. In another aspect, X and Y are each CH; and R₂ is alkyl. In another aspect, X and Y are each CH; and R₂ is isopropyl. In another aspect, X and Y are each CH; R₂ is optionally substituted alkyl, and R₃ is OH. In another aspect, X and Y are each CH; R₂ is alkyl, and R₃ is OH. In another aspect, X and Y are each CH; R₂ is isopropyl, and R₃ is OH. In another aspect, R₆ is hydrogen. In another aspect, X and Y are each CH; R₂ is optionally substituted alkyl; and R₆ is hydrogen. In another aspect, X and Y are each CH; R₂ is optionally substituted alkyl; R₃ is OH; and R₆ is hydrogen. In another aspect, X and Y are each CH; R₂ is alkyl; and R₆ is hydrogen. In another aspect, X and Y are each CH; R₂ is alkyl; R₃ is OH; and R₆ is hydrogen. In another aspect, X and Y are each CH; R₂ is isopropyl; and R₆ is hydrogen. In another aspect, X and Y are each CH; R₂ is isopropyl; R₃ is OH; and R₆ is hydrogen. In another aspect, R₄ is fluoroalkoxy containing 1-5 fluorines. In another aspect, R₅ is fluoroalkoxy containing 1-5 fluorines. In another aspect, R₄ and R₅ are each fluoroalkoxy containing 1-5 fluorines. In another aspect, R₄ and R₅ are each fluoroalkoxy containing 1-5 fluorines; and R₂ is optionally substituted alkyl. In another aspect, R₄ and R₅ are each fluoroalkoxy containing 1-5 fluorines; and R₂ is alkyl. In another aspect, R₄ and R₅ are each fluoroalkoxy containing 1-5 fluorines; and R₂ is isopropyl. In another aspect, R₄ and R₅ are each fluoroalkoxy containing 1-5 fluorines; and R₃ is OH. In another aspect, R₄ and R₅ are each fluoroalkoxy containing 1-5 fluorines; R₃ is OH; and R₂ is optionally substituted alkyl. In another aspect, R₄ and R₅ are each fluoroalkoxy containing 1-5 fluorines; R₃ is OH; and R₂ is alkyl. In another aspect, R₄ and R₅ are each fluoroalkoxy containing 1-5 fluorines; R₃ is OH; and R₂ is isopropyl. In another aspect, R₄ and R₅ are each fluoroalkoxy containing 1-5 fluorines; X and Y are each CH; and R₂ is optionally substituted alkyl. In another aspect, R₄ and R₅ are each fluoroalkoxy containing 1-5 fluorines; X and Y are each CH; and R₂ is alkyl. In another aspect, R₄ and R₅ are each fluoroalkoxy containing 1-5 fluorines; X and Y are each CH; and R₂ is isopropyl. In another aspect, R₄ and R₅ are each fluoroalkoxy containing 1-5 fluorines; R₃ is OH; X and Y are each CH; and R₂ is optionally substituted alkyl. In another aspect, $R_4$ and $R_5$ are each fluoroalkoxy containing 1-5 fluorines; $R_3$ is OH; X and Y are each CH; and $R_2$ is alkyl. In another aspect, $R_4$ and $R_5$ are each fluoroalkoxy containing 1-5 fluorines; $R_3$ is OH; X and Y are each CH; and $R_2$ is isopropyl. In another aspect, $R_4$ and $R_5$ are each fluoroalkoxy containing 1-5 fluorines; and $R_6$ is hydrogen. In another aspect, $R_4$ and $R_5$ are each fluoroalkoxy containing 1-5 fluorines; $R_6$ is hydrogen; and $R_2$ is optionally substituted alkyl. In another aspect, $R_4$ and $R_5$ are each fluoroalkoxy containing 1-5 fluorines; $R_6$ is hydrogen; and $R_2$ is alkyl. In another aspect, $R_4$ and $R_5$ are each fluoroalkoxy containing 1-5 fluorines; $R_6$ is hydrogen; and $R_2$ is isopropyl. In another aspect, $R_4$ and $R_5$ are each fluoroalkoxy containing 1-5 fluorines; X and Y are each CH; $R_6$ is hydrogen; and $R_2$ is optionally substituted alkyl. In another aspect, $R_4$ and $R_5$ are each fluoroalkoxy containing 1-5 fluorines; X and Y are each CH; $R_6$ is hydrogen; and $R_2$ is alkyl. In another aspect, $R_4$ and $R_5$ are each fluoroalkoxy containing 1-5 fluorines; X and Y are each CH; $R_6$ is hydrogen; and $R_2$ is isopropyl. In another aspect, $R_4$ and $R_5$ are each fluoroalkoxy containing 1-5 fluorines; X and Y are each CH; $R_3$ is OH; $R_6$ is hydrogen; and $R_2$ is optionally substituted alkyl. In another aspect, $R_4$ and $R_5$ are each fluoroalkoxy containing 1-5 fluorines; X and Y are each CH; $R_3$ is OH; $R_6$ is hydrogen; and $R_2$ is alkyl. In another aspect, $R_4$ and $R_5$ are each fluoroalkoxy containing 1-5 fluorines; X and Y are each CH; $R_3$ is OH; $R_6$ is hydrogen; and $R_2$ is isopropyl.

In another aspect, the compound of Formula (I) or (II) is

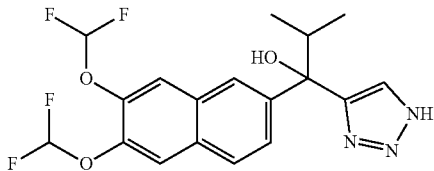 [SMILES: CC(C)C(O)(c1ccc2cc(OC(F)F)c(OC(F)F)cc2c1)c1c[nH]nn1]

(also known as seviteronel), or a pharmaceutically acceptable salt thereof.

In one aspect, the invention provides a method of treating a subject suffering from or susceptible to a brain tumor, the method comprising the administration of radiation therapy and an effective amount of a seviteronel, or pharmaceutically acceptable salt thereof. In another aspect, seviteronel, or pharmaceutically acceptable salt thereof, and radiation therapy are administered concurrently. In another aspect, seviteronel, or pharmaceutically acceptable salt thereof, and radiation therapy are administered sequentially.

In one aspect, the invention provides a method of treating a subject suffering from or susceptible to a brain tumor, the method comprising the administration of radiation therapy and an effective amount of a pharmaceutical composition comprising: (1) seviteronel, or a pharmaceutically acceptable salt thereof, and (2) a pharmaceutically acceptable carrier. In another aspect, the pharmaceutical composition comprising seviteronel, or pharmaceutically acceptable salt thereof, and a pharmaceutically acceptable carrier and radiation therapy are administered concurrently. In another aspect, the pharmaceutical composition comprising seviteronel, or pharmaceutically acceptable salt thereof and a pharmaceutically acceptable carrier and radiation therapy are administered sequentially.

In another aspect, the method further comprises the administration of dexamethasone. In another aspect, the seviteronel and dexamethasone are administered concurrently. In another aspect, the seviteronel and dexamethasone are administered sequentially. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 150 mg-750 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In another aspect, the invention provides a method of treating a subject suffering from or susceptible to a brain tumor, the method comprising the administration of radiation therapy and an effective amount of a pharmaceutical composition comprising: (1) seviteronel, or a pharmaceutically acceptable salt thereof, (2) dexamethasone, or a pharmaceutically acceptable salt thereof, and (3) a pharmaceutically acceptable carrier. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 150 mg-750 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In another aspect, the invention provides a pharmaceutical composition comprising: (1) seviteronel, or a pharmaceutically acceptable salt thereof, (2) dexamethasone, or a pharmaceutically acceptable salt thereof, and (3) a pharmaceutically acceptable carrier for use in treating a subject suffering from or susceptible to a brain tumor. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 150 mg-750 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In any of the embodiments presented herein, the brain tumor is a brain cancer. In any of the embodiments presented herein, the brain tumor is of brain tissue origin. In any of the embodiments presented herein, the brain tumor is not of brain tissue origin (i.e., tumors that originate outside of the brain and metastasize to the brain). In any of the embodiments presented herein, the brain tumor is of lung, breast, skin (e.g., melanoma), colon, or kidney tissue origin. In any of the embodiments presented herein, the brain tumor is androgen positive. In any of the embodiments presented herein, the brain tumor is CYP17 positive. In any of the embodiments presented herein, the brain tumor is androgen positive and CYP17 positive. In another aspect, the brain cancer is androgen receptor positive. In any of the embodiments presented herein, the brain cancer is CYP17 positive. In any of the embodiments presented herein, the brain cancer is androgen positive and CYP17 positive. In another aspect, the brain cancer is a glioma, a meningioma, or a medulloblastoma. In another aspect, the brain cancer is a glioma. In another aspect, the glioma is a glioblastoma, an astrocytoma, an oligodendroglioma, or an ependyoma. In another aspect, the glioma is glioblastoma multiforme (GBM).

In certain instances, the compounds of the invention are selected from the following (and pharmaceutically acceptable salts, solvates, or hydrates thereof):

1-(6,7-Dimethoxynaphthalen-2-yl)-2-methyl-1-(1H-1,2,3-triazol-4-yl)propan-1-ol (1);

1-(6,7-Dimethoxyisoquinolin-3-yl)-2-methyl-1-(1H-1,2,3-triazol-4-yl)propan-1-ol (2);

1-(6,7-Bis(difluoromethoxy)naphthalen-2-yl)-2-methyl-1-(1H-1,2,3-triazol-4-yl)propan-1-ol (3);

2-Methyl-1-(6-(oxazol-5-yl)naphthalen-2-yl)-1-(1H-1,2,3-triazol-4-yl)propan-1-ol (4);

1-(6,7-Dichloroquinolin-2-yl)-2-methyl-1-(1H-1,2,3-triazol-4-yl)propan-1-ol (5);

1-(6-Chloro-5-(trifluoromethyl) quinolin-2-yl)-2-methyl-1-(1H-1,2,3-triazol-4-yl) propan-1-ol (6);

2-Methyl-1-(6-(methylthio) quinolin-2-yl)-1-(1H-1,2,3-triazol-4-yl) propan-1-ol (7);

1-(6-Cyclopropoxyquinolin-2-yl)-2-methyl-1-(1H-1,2,3-triazol-4-yl)propan-1-ol (8);

1-(7-Chloro-6-(trifluoromethyl) quinolin-2-yl)-2-methyl-1-(1H-1,2,3-triazol-4-yl) propan-1-ol (9);

1-(6-(Difluoromethoxy)-5-(thiophen-2-yl)quinolin-2-yl)-2-methyl-1-(1H-1,2,3-triazol-4-yl)propan-1-ol (10);
2-Methyl-1-(5-(thiophen-2-yl)-6-(2,2,2-trifluoroethoxy)quinolin-2-yl)-1-(1H-1,2,3-triazol-5-yl)propan-1-ol (11)
2-methyl-1-(1H-1,2,3-triazol-4-yl)-1-(6-(2,2,2-trifluoroethoxy)naphthalen-2-yl)propan-1-ol (12)
1-(6-(difluoromethoxy)naphthalen-2-yl)-2-methyl-1-(1H-1,2,3-triazol-4-yl)propan-1-ol (13)
1-(6-methoxyquinolin-2-yl)-2-methyl-1-(1H-1,2,3-triazol-4-yl)propan-1-ol (14)
2-methyl-1-(1H-1,2,3-triazol-4-yl)-1-(6-(2,2,2-trifluoroethoxy)quinolin-2-yl)propan-1-ol (15)
1-(6,7-difluoroquinolin-2-yl)-2-methyl-1-(1H-1,2,3-triazol-4-yl)propan-1-ol (16)
2-methyl-1-(1H-1,2,3-triazol-4-yl)-1-(6-(trifluoromethoxy)quinolin-2-yl)propan-1-ol (17)
1-(5,6-dichloroquinolin-2-yl)-2-methyl-1-(1H-1,2,3-triazol-4-yl)propan-1-ol (18)
1-(5-chloro-6-(difluoromethoxy)quinolin-2-yl)-2-methyl-1-(1H-1,2,3-triazol-4-yl)propan-1-ol (19)
1-(6,7-bis(difluoromethoxy)quinolin-2-yl)-2-methyl-1-(1H-1,2,3-triazol-4-yl)propan-1-ol (20)
1-(5-chloro-6-(trifluoromethoxy)quinolin-2-yl)-2-methyl-1-(1H-1,2,3-triazol-4-yl)propan-1-ol (21)
1-(6-(4-fluorophenyl)-5-(trifluoromethyl)quinolin-2-yl)-2-methyl-1-(1H-1,2,3-triazol-4-yl)propan-1-ol (22)
2-(1-hydroxy-2-methyl-1-(1H-1,2,3-triazol-4-yl)propyl)-5-(trifluoromethyl)quinoline-6-carbonitrile (23).

In one aspect, the invention provides a method of treating a subject suffering from or susceptible to a disorder or disease delineated herein, comprising administering to the subject an effective amount of a compound or pharmaceutical composition described herein.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which.

DETAILED DESCRIPTION

Definitions

Figure 1:
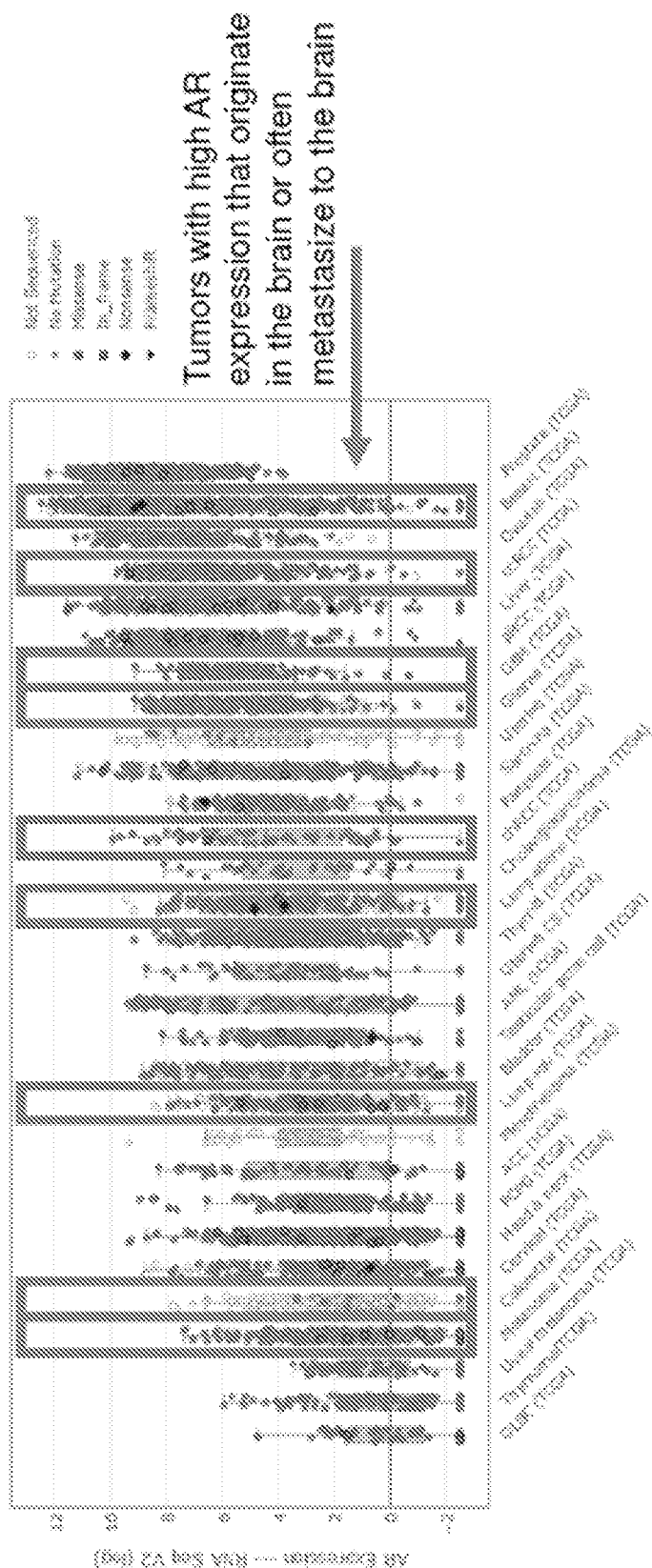
FIG. 1. depicts the androgen receptor (AR) expression levels across various tumor types, including those which originate in the brain and those that often metastasize to the brain.

In order that the invention may be more readily understood, certain terms are first defined here for convenience.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes blocking, inhibiting, attenuating, protecting against, modulating, reversing the effects of and reducing the occurrence of e.g., the harmful effects of a disorder.

As used herein, "radiation therapy" is treatment using ionizing radiation where the ionizing radiation is made up of energetic subatomic particles, ions, or atoms and electromagnetic waves where ionization of cancer cell components may occur via indirect or direct ionization.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "tumor" refers to a swelling of a part of the body, generally without inflammation, caused by an abnormal growth of tissue, whether benign or malignant.

The term "brain tumor" refers to growth of abnormal cells in the tissues of the brain and can be benign or malignant. Thus, the term "brain tumor" as used herein encompasses tissue growth in the brain irrespective of tissue origin.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "percent colony formation" as used herein is the number of colonies after treatment with seviteronel and normalized to the number of colonies formed in the absence of seviteronel.

The term "surviving fraction" as used herein is the fraction of cells that retain their reproductive integrity after radiation normalized to the fraction of cells seeded and the colonies formed in the absence of irradiation The term "enhancement ratio" as used herein is the ratio of the Dmid (the area under the radiation survival curve, which reflects the effectiveness of radiation) in the absence of seviteronel divided by the Dmid in the presence of seviteronel.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore the compounds of the invention include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" (or plus and minus) configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

The term "haloalkoxy" refers to an —O-alkyl radical that is substituted by one or more halo substituents. Examples of haloalkoxy groups include trifluoromethoxy, and 2,2,2-trifluoroethoxy.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolanyl, tetrahydrofuranyl, tetrahydrothienyl, thienyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, haloalkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, mercaptoalkoxy, N-hydroxyamidinyl, or N'-aryl, N''-hydroxyamidinyl.

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd.; Jähnisch, K et al, *Angew. Chem. Int. Ed. Engl.* 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

In one aspect, the invention provides a method of treating a subject suffering from or susceptible to a brain tumor, the method comprising the administration of radiation therapy and an effective amount of: 1) a compound of Formula (I), or pharmaceutically acceptable salt thereof; or 2) a pharmaceutical composition comprising a compound of Formula (I), or a pharmaceutically acceptable salt thereof, and a pharmaceutically acceptable carrier:

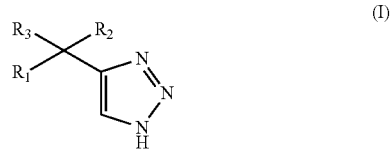

each $R_1$ and $R_2$ is independently optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl; and $R_3$ is H, OH, alkoxy, amino, alkylamino, or dialkylamino. In another aspect, the compound of Formula (I), or pharmaceutically acceptable salt thereof, and radiation therapy are administered concurrently. In another aspect, the compound of Formula (I), or pharmaceutically acceptable salt thereof, and radiation therapy are administered sequentially.

In one aspect, the invention provides a method of treating a subject suffering from or susceptible to a brain tumor, the method comprising the administration of radiation therapy and an effective amount of a compound of Formula (I), or pharmaceutically acceptable salt thereof:

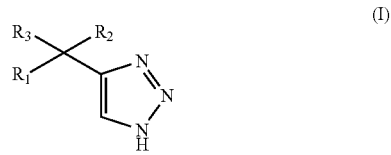

each $R_1$ and $R_2$ is independently optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl; and $R_3$ is H, OH, alkoxy, amino, alkylamino, or dialkylamino. In another aspect, the compound of Formula (I), or pharmaceutically acceptable salt thereof, and radiation therapy are administered concurrently. In another aspect, the compound of Formula (I), or pharmaceutically acceptable salt thereof, and radiation therapy are administered sequentially.

In one aspect, the invention provides a method of treating a subject suffering from or susceptible to a brain tumor, the method comprising the administration of radiation therapy and an effective amount of a pharmaceutical composition comprising: 1) a compound of Formula (I), or a pharmaceutically acceptable salt thereof, and (2) a pharmaceutically acceptable carrier:

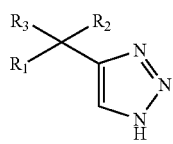

(I)

each $R_1$ and $R_2$ is independently optionally substituted aryl, optionally substituted naphthyl, optionally substituted heteroaryl, optionally substituted alkyl, optionally substituted aralkyl, optionally substituted cycloalkyl, optionally substituted heterocycloalkyl, optionally substituted heteroaryl-alkyl or optionally substituted heteroaryl-(di)fluoroalkyl; and $R_3$ is H, OH, alkoxy, amino, alkylamino, or dialkylamino. In another aspect, the pharmaceutical composition comprising the compound of Formula (I), or pharmaceutically acceptable salt thereof, and radiation therapy are administered concurrently. In another aspect, the pharmaceutical composition comprising the compound of Formula (I), or pharmaceutically acceptable salt thereof, and radiation therapy are administered sequentially.

In another aspect, $R_3$ is OH.

In another aspect, $R_2$ is optionally substituted alkyl and $R_3$ is OH.

In another aspect, $R_1$ is optionally substituted aryl, $R_2$ is alkyl, and $R_3$ is OH.

In another aspect, $R_1$ is substituted aryl, $R_2$ is alkyl, and $R_3$ is OH.

In another aspect, $R_1$ is optionally substituted naphthyl, $R_2$ is alkyl, and $R_3$ is OH.

In another aspect, $R_1$ is substituted naphthyl, $R_2$ is alkyl, and $R_3$ is OH.

In another aspect, $R_1$ is naphthyl substituted with 1, 2, 3 or 4 substituents, independently selected from alkyl, alkoxy, haloalkoxy, cyano, halo, amino, mono-alkylamino, di-alkylamino, or heteroaryl.

In another aspect, $R_1$ is naphthyl substituted with 1, 2, 3 or 4 substituents, independently selected from alkyl, alkoxy, haloalkoxy, cyano, halo, amino, mono-alkylamino, di-alkylamino, or heteroaryl, $R_2$ is alkyl, and $R_3$ is OH.

In another aspect, the compound of Formula (I) is of Formula (II), or a pharmaceutically acceptable salt thereof:

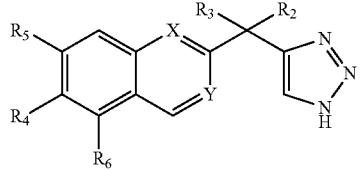

(II)

wherein X is CH or N; Y is CH or N; and $R_4$, $R_5$ and $R_6$ are each independently H, halogen, alkoxy, alkylthio, cycloalkoxy, fluoroalkoxy containing 1-5 fluorines, fluoroalkyl containing 1-5 fluorines, cyano, carboxamido, optionally substituted aryl, or optionally substituted heteroaryl. In another aspect, X is CH. In another aspect, X is N. In another aspect, Y is CH. In another aspect, Y is N. In another aspect, X and Y are each CH. In another aspect, X is NH and Y is CH. In another aspect, $R_2$ is optionally substituted alkyl. In another aspect, $R_2$ is alkyl. In another aspect, $R_2$ is isopropyl. In another aspect, $R_3$ is OH. In another aspect, X and Y are each CH; and $R_2$ is optionally substituted alkyl. In another aspect, X and Y are each CH; and $R_2$ is alkyl. In another aspect, X and Y are each CH; and $R_2$ is isopropyl. In another aspect, X and Y are each CH; $R_2$ is optionally substituted alkyl, and $R_3$ is OH. In another aspect, X and Y are each CH; $R_2$ is alkyl, and $R_3$ is OH. In another aspect, X and Y are each CH; $R_2$ is isopropyl, and $R_3$ is OH. In another aspect, $R_6$ is hydrogen. In another aspect, X and Y are each CH; $R_2$ is optionally substituted alkyl; and $R_6$ is hydrogen. In another aspect, X and Y are each CH; $R_2$ is optionally substituted alkyl; $R_3$ is OH; and $R_6$ is hydrogen. In another aspect, X and Y are each CH; $R_2$ is alkyl; and $R_6$ is hydrogen. In another aspect, X and Y are each CH; $R_2$ is alkyl; $R_3$ is OH; and $R_6$ is hydrogen. In another aspect, X and Y are each CH; $R_2$ is isopropyl; and $R_6$ is hydrogen. In another aspect, X and Y are each CH; $R_2$ is isopropyl; $R_3$ is OH; and $R_6$ is hydrogen. In another aspect, $R_4$ is fluoroalkoxy containing 1-5 fluorines. In another aspect, $R_5$ is fluoroalkoxy containing 1-5 fluorines. In another aspect, $R_4$ and $R_5$ are each fluoroalkoxy containing 1-5 fluorines. In another aspect, $R_4$ and $R_5$ are each fluoroalkoxy containing 1-5 fluorines; and $R_2$ is optionally substituted alkyl. In another aspect, $R_4$ and $R_5$ are each fluoroalkoxy containing 1-5 fluorines; and $R_2$ is alkyl. In another aspect, $R_4$ and $R_5$ are each fluoroalkoxy containing 1-5 fluorines; and $R_2$ is isopropyl. In another aspect, $R_4$ and $R_5$ are each fluoroalkoxy containing 1-5 fluorines; and $R_3$ is OH. In another aspect, $R_4$ and $R_5$ are each fluoroalkoxy containing 1-5 fluorines; $R_3$ is OH; and $R_2$ is optionally substituted alkyl. In another aspect, $R_4$ and $R_5$ are each fluoroalkoxy containing 1-5 fluorines; $R_3$ is OH; and $R_2$ is alkyl. In another aspect, $R_4$ and $R_5$ are each fluoroalkoxy containing 1-5 fluorines; $R_3$ is OH; and $R_2$ is isopropyl. In another aspect, $R_4$ and $R_5$ are each fluoroalkoxy containing 1-5 fluorines; X and Y are each CH; and $R_2$ is optionally substituted alkyl. In another aspect, $R_4$ and $R_5$ are each fluoroalkoxy containing 1-5 fluorines; X and Y are each CH; and $R_2$ is alkyl. In another aspect, $R_4$ and $R_5$ are each fluoroalkoxy containing 1-5 fluorines; X and Y are each CH; and $R_2$ is isopropyl. In another aspect, $R_4$ and $R_5$ are each fluoroalkoxy containing 1-5 fluorines; $R_3$ is OH; X and Y are each CH; and $R_2$ is optionally substituted alkyl. In another aspect, $R_4$ and $R_5$ are each fluoroalkoxy containing 1-5 fluorines; $R_3$ is OH; X and Y are each CH; and $R_2$ is alkyl. In another aspect, $R_4$ and $R_5$ are each fluoroalkoxy containing 1-5 fluorines; $R_3$ is OH; X and Y are each CH; and $R_2$ is isopropyl. In another aspect, $R_4$ and $R_5$ are each fluoroalkoxy containing 1-5 fluorines; and $R_6$ is hydrogen. In another aspect, $R_4$ and $R_5$ are each fluoroalkoxy containing 1-5 fluorines; $R_6$ is hydrogen; and $R_2$ is optionally substituted alkyl. In another aspect, $R_4$ and $R_5$ are each fluoroalkoxy containing 1-5 fluorines; $R_6$ is hydrogen; and $R_2$ is alkyl. In another aspect, $R_4$ and $R_5$ are each fluoroalkoxy containing 1-5 fluorines; $R_6$ is hydrogen; and $R_2$ is isopropyl. In another aspect, $R_4$ and $R_5$ are each fluoroalkoxy containing 1-5 fluorines; X and Y are each CH; $R_6$ is hydrogen; and $R_2$ is optionally substituted alkyl. In another aspect, $R_4$ and $R_5$ are each fluoroalkoxy containing 1-5 fluorines; X and Y are each CH; $R_6$ is hydrogen; and $R_2$ is alkyl. In another aspect, $R_4$ and $R_5$ are each fluoroalkoxy containing 1-5 fluorines; X and Y are each CH; $R_6$ is hydrogen; and $R_2$ is isopropyl. In another aspect, $R_4$ and $R_5$ are each fluoroalkoxy containing 1-5 fluorines; X and Y are each CH; $R_3$ is OH; $R_6$ is hydrogen; and $R_2$ is optionally substituted alkyl. In another aspect, $R_4$ and $R_5$ are each fluoroalkoxy containing 1-5 fluorines; X and Y are each CH; $R_3$ is OH; $R_6$ is hydrogen; and $R_2$ is alkyl. In another aspect, $R_4$ and $R_5$ are each fluoroalkoxy containing 1-5 fluorines; X and Y are each CH; $R_3$ is OH; $R_6$ is hydrogen; and $R_2$ is isopropyl.

In another aspect, the compound of Formula (I) or (II) is

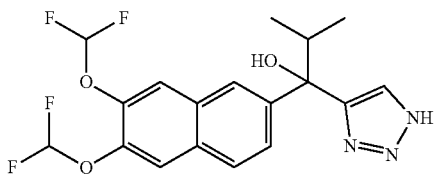 [SMILES: CC(C)C(O)(c1ccc2cc(OC(F)F)c(OC(F)F)cc2c1)c1c[nH]nn1]

(also known as seviteronel), or a pharmaceutically acceptable salt thereof.

In one aspect, the invention provides a method of treating a subject suffering from or susceptible to a brain tumor, the method comprising the administration of radiation therapy and an effective amount of a seviteronel, or pharmaceutically acceptable salt thereof. In another aspect, seviteronel, or pharmaceutically acceptable salt thereof, and radiation therapy are administered concurrently. In another aspect, seviteronel, or pharmaceutically acceptable salt thereof, and radiation therapy are administered sequentially.

In one aspect, the invention provides a method of treating a subject suffering from or susceptible to a brain tumor, the method comprising the administration of radiation therapy and an effective amount of a pharmaceutical composition comprising: (1) seviteronel, or a pharmaceutically acceptable salt thereof, and (2) a pharmaceutically acceptable carrier. In another aspect, the pharmaceutical composition comprising seviteronel, or pharmaceutically acceptable salt thereof, and a pharmaceutically acceptable carrier and radiation therapy are administered concurrently. In another aspect, the pharmaceutical composition comprising seviteronel, or pharmaceutically acceptable salt thereof and a pharmaceutically acceptable carrier and radiation therapy are administered sequentially.

In another aspect, the method further comprises the administration of dexamethasone. In another aspect, the seviteronel and dexamethasone are administered concurrently. In another aspect, the seviteronel and dexamethasone are administered sequentially. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 150 mg-750 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In another aspect, the invention provides a method of treating a subject suffering from or susceptible to a brain tumor, the method comprising the administration of radiation therapy, an effective amount of a pharmaceutical composition comprising: (1) seviteronel, or a pharmaceutically acceptable salt thereof, and (2) dexamethasone, or a pharmaceutically acceptable salt thereof, and (3) a pharmaceutically acceptable carrier. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 150 mg-750 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In another aspect, the invention provides a pharmaceutical composition comprising: (1) seviteronel, or a pharmaceutically acceptable salt thereof, (2) dexamethasone, or a pharmaceutically acceptable salt thereof, and (3) a pharmaceutically acceptable carrier for use in treating a subject suffering from or susceptible to a brain tumor. In another aspect, the invention provides a pharmaceutical composition comprising: (1) seviteronel, or a pharmaceutically acceptable salt thereof, and (2) a pharmaceutically acceptable carrier for use in treating a subject suffering from or susceptible to a brain tumor. In another aspect, the invention provides a pharmaceutical composition comprising: (1) a compound of Formula (I), or a pharmaceutically acceptable salt thereof, and (2) a pharmaceutically acceptable carrier for use in treating a subject suffering from or susceptible to a brain tumor. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 150 mg-750 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In any of the embodiments presented herein, the brain tumor is a brain cancer. In any of the embodiments presented herein, the brain tumor is of brain tissue origin. In any of the embodiments presented herein, the brain tumor is not of brain tissue origin (i.e., tumors that originate outside of the brain and metastasize to the brain). In any of the embodiments presented herein, the brain tumor is of lung, breast, skin (e.g., melanoma), colon, or kidney tissue origin. In any of the embodiments presented herein, the brain tumor is androgen positive. In any of the embodiments presented herein, the brain tumor is CYP17 positive. In any of the embodiments presented herein, the brain tumor is androgen positive and CYP17 positive. In another aspect, the brain cancer is androgen receptor positive. In any of the embodiments presented herein, the brain cancer is CYP17 positive. In any of the embodiments presented herein, the brain cancer is androgen positive and CYP17 positive. In another aspect, the brain cancer is a glioma, a meningioma, or a medulloblastoma. In another aspect, the brain cancer is a glioma. In another aspect, the glioma is a glioblastoma, an astrocytoma, an oligodendroglioma, or an ependyoma. In another aspect, the glioma is glioblastoma multiforme (GBM).

In certain instances, the compounds of the invention are selected from the following (and pharmaceutically acceptable salts, solvates, or hydrates thereof):

1-(6,7-Dimethoxynaphthalen-2-yl)-2-methyl-1-(1H-1,2,3-triazol-4-yl)propan-1-ol (1);
1-(6,7-Dimethoxyisoquinolin-3-yl)-2-methyl-1-(1H-1,2,3-triazol-4-yl)propan-1-ol (2);
1-(6,7-Bis(difluoromethoxy)naphthalen-2-yl)-2-methyl-1-(1H-1,2,3-triazol-4-yl)propan-1-ol (3);
2-Methyl-1-(6-(oxazol-5-yl)naphthalen-2-yl)-1-(1H-1,2,3-triazol-4-yl)propan-1-ol (4);
1-(6,7-Dichloroquinolin-2-yl)-2-methyl-1-(1H-1,2,3-triazol-4-yl)propan-1-ol (5);
1-(6-Chloro-5-(trifluoromethyl) quinolin-2-yl)-2-methyl-1-(1H-1,2,3-triazol-4-yl) propan-1-ol (6);
2-Methyl-1-(6-(methylthio) quinolin-2-yl)-1-(1H-1,2,3-triazol-4-yl) propan-1-ol (7);
1-(6-Cyclopropoxyquinolin-2-yl)-2-methyl-1-(1H-1,2,3-triazol-4-yl)propan-1-ol (8);
1-(7-Chloro-6-(trifluoromethyl) quinolin-2-yl)-2-methyl-1-(1H-1,2,3-triazol-4-yl) propan-1-ol (9);
1-(6-(Difluoromethoxy)-5-(thiophen-2-yl)quinolin-2-yl)-2-methyl-1-(1H-1,2,3-triazol-4-yl)propan-1-ol (10);
2-Methyl-1-(5-(thiophen-2-yl)-6-(2,2,2-trifluoroethoxy)quinolin-2-yl)-1-(1H-1,2,3-triazol-5-yl)propan-1-ol (11)
2-methyl-1-(1H-1,2,3-triazol-4-yl)-1-(6-(2,2,2-trifluoroethoxy)naphthalen-2-yl)propan-1-ol (12)
1-(6-(difluoromethoxy)naphthalen-2-yl)-2-methyl-1-(1H-1,2,3-triazol-4-yl)propan-1-ol (13)
1-(6-methoxyquinolin-2-yl)-2-methyl-1-(1H-1,2,3-triazol-4-yl)propan-1-ol (14)
2-methyl-1-(1H-1,2,3-triazol-4-yl)-1-(6-(2,2,2-trifluoroethoxy)quinolin-2-yl)propan-1-ol (15)
1-(6,7-difluoroquinolin-2-yl)-2-methyl-1-(1H-1,2,3-triazol-4-yl)propan-1-ol (16)

2-methyl-1-(1H-1,2,3-triazol-4-yl)-1-(6-(trifluoromethoxy)
quinolin-2-yl)propan-1-ol (17)
1-(5,6-dichloroquinolin-2-yl)-2-methyl-1-(1H-1,2,3-triazol-4-yl)propan-1-ol (18)
1-(5-chloro-6-(difluoromethoxy)quinolin-2-yl)-2-methyl-1-(1H-1,2,3-triazol-4-yl)propan-1-ol (19)
1-(6,7-bis(difluoromethoxy)quinolin-2-yl)-2-methyl-1-(1H-1,2,3-triazol-4-yl)propan-1-ol (20)
1-(5-chloro-6-(trifluoromethoxy)quinolin-2-yl)-2-methyl-1-(1H-1,2,3-triazol-4-yl)propan-1-ol (21)
1-(6-(4-fluorophenyl)-5-(trifluoromethyl)quinolin-2-yl)-2-methyl-1-(1H-1,2,3-triazol-4-yl)propan-1-ol (22)
2-(1-hydroxy-2-methyl-1-(1H-1,2,3-triazol-4-yl)propyl)-5-(trifluoromethyl)quinoline-6-carbonitrile (23).

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

In one aspect, the invention provides a method of treating a subject suffering from or susceptible to a disorder or disease delineated herein, comprising administering to the subject an effective amount of a compound or pharmaceutical composition described herein.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Pharmaceutical Compositions

In one aspect, the invention provides a treatment regime of radiation therapy and a pharmaceutical composition comprising: 1) seviteronel, or salt thereof; 2) dexamethasone, or salt thereof; and 3) a pharmaceutically acceptable carrier. In another aspect, the amount of seviteronel in the composition is in a range of about 150 mg-750 mg. In another aspect, the amount of seviteronel in the composition is in a range of about 400 mg-650 mg. In another aspect, the amount of seviteronel in the composition is 600 mg. In another aspect, the amount of seviteronel in the composition is 450 mg. In another aspect, the amount of dexamethasone in the composition is in a range of about 0.25 mg-1000 mg. In another aspect, the amount of dexamethasone in the composition is in a range of about 0.40 mg-0.60 mg. In another aspect, the amount of dexamethasone in the composition is 0.5 mg. In another aspect, the amount of seviteronel in the composition is in a range of about 150 mg-750 mg, and the amount of dexamethasone in the composition is in a range of about 0.25 mg-1000 mg. In another aspect, the amount of seviteronel in the composition is in a range of about 150 mg-750 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is in a range of about 400 mg-650 mg, and the amount of dexamethasone in the composition is in a range of about 0.25 mg-1000 mg. In another aspect, the amount of seviteronel in the composition is in a range of about 400 mg-650 mg, and the amount of dexamethasone in the composition is in a range of about 0.40 mg-0.60 mg. In another aspect, the amount of seviteronel in the composition is in a range of about 400 mg-650 mg, and the amount of dexamethasone in the composition is 0.5 mg. In another aspect, the amount of seviteronel in the composition is in a range of about 400 mg-650 mg, and the amount of dexamethasone in the composition is 0.5 mg. In another aspect, the amount of seviteronel in the composition is 600 mg, and the amount of dexamethasone in the composition is in a range of about 0.25 mg-1000 mg. In another aspect, the amount of seviteronel in the composition is 600 mg, and the amount of dexamethasone in the composition is in a range of about 0.40 mg-0.60 mg. In another aspect, the amount of seviteronel in the composition is 600 mg, and the amount of dexamethasone in the composition is 0.5 mg. In another aspect, the amount of seviteronel in the composition is 450 mg, and the amount of dexamethasone in the composition is in a range of about 0.25 mg-1000 mg. In another aspect, the amount of seviteronel in the composition is 450 mg, and the amount of dexamethasone in the composition is in a range of about 0.40 mg-0.60 mg. In another aspect, the amount of seviteronel in the composition is 450 mg, and the amount of dexamethasone in the composition is 0.5 mg.

In one aspect, the invention provides a dosing regimen comprising: 1) seviteronel, or salt thereof; and 2) dexamethasone, or salt thereof. In another aspect, the amount of seviteronel is in a range of about 150 mg-750 mg. In another aspect, the amount of seviteronel is in a range of about 400 mg- 650 mg. In another aspect, the amount of seviteronel is 600 mg. In another aspect, the amount of seviteronel is 450 mg. In another aspect, the amount of dexamethasone is in a range of about 0.25 mg-1000 mg. In another aspect, the amount of dexamethasone is in a range of about 0.40 mg-0.60 mg. In another aspect, the amount of dexamethasone is 0.5 mg. In another aspect, the amount of seviteronel in is in a range of about 150 mg-750 mg, and the amount of dexamethasone is in a range of about 0.25 mg-1000 mg. In another aspect, the amount of seviteronel is in a range of about 150 mg-750 mg, and the amount of dexamethasone is in a range of about 0.40 mg-0.60 mg. In another aspect, the amount of seviteronel is in a range of about 400 mg-650 mg, and the amount of dexamethasone is 0.5 mg. In another aspect, the amount of seviteronel is in a range of about 400 mg-650 mg, and the amount of dexamethasone is in a range of about 0.25 mg-1000 mg. In another aspect, the amount of seviteronel is in a range of about 400 mg-650 mg, and the amount of dexamethasone is in a range of about 0.40 mg-0.60 mg. In another aspect, the amount of seviteronel is in a range of about 400 mg-650 mg, and the amount of dexamethasone is 0.5 mg. In another aspect, the amount of seviteronel is in a range of about 400 mg-650 mg, and the amount of dexamethasone is 0.5 mg. In another aspect, the amount of seviteronel is 600 mg, and the amount of dexamethasone is in a range of about 0.25 mg-1000 mg. In another aspect, the amount of seviteronel is 600 mg, and the amount of dexamethasone is in a range of about 0.40 mg-0.60 mg. In another aspect, the amount of seviteronel is 600 mg, and the amount of dexamethasone is 0.5 mg. In another aspect, the amount of seviteronel is 450 mg, and the amount of dexamethasone is in a range of about 0.25 mg-1000 mg. In another aspect, the amount of seviteronel is 450 mg, and the amount of dexamethasone is in a range of about 0.40 mg-0.60 mg. In another aspect, the amount of seviteronel is 450 mg, and the amount of dexamethasone is 0.5 mg. In another aspect, seviteronel and dexamethasone are administered concurrently. In another aspect, seviteronel and dexamethasone are administered sequentially.

In one aspect, the invention provides a pharmaceutical composition comprising any compound(s) described herein.

In one aspect, the invention provides a kit comprising an effective amount of any compound(s) described herein, or combinations thereof, in unit dosage form, together with instructions for administering the compound to a subject suffering from or susceptible to a brain tumor. In any of the embodiments presented herein, the brain tumor is a brain cancer. In any of the embodiments presented herein, the brain tumor is of brain tissue origin. In any of the embodiments presented herein, the brain tumor is not of brain tissue origin (i.e., tumors that originate outside of the brain and metastasize to the brain). In any of the embodiments presented herein, the brain tumor is of lung, breast, skin (e.g., melanoma), colon, or kidney tissue origin. In any of the embodiments presented herein, the brain tumor is androgen positive. In any of the embodiments presented herein, the brain tumor is CYP17 positive. In any of the embodiments presented herein, the brain tumor is androgen positive and CYP17 positive. In another aspect, the brain cancer is androgen receptor positive. In any of the embodiments presented herein, the brain cancer is CYP17 positive. In any of the embodiments presented herein, the brain cancer is androgen positive and CYP17 positive. In another aspect, the brain cancer is a glioma, a meningioma, or a medulloblastoma. In another aspect, the brain cancer is a glioma. In another aspect, the glioma is a glioblastoma, an astrocytoma, an oligodendroglioma, or an ependyoma. In another aspect, the glioma is glioblastoma multiforme (GBM).

In one aspect, the invention provides a kit comprising an effective amount of any compound(s) described herein, or combinations thereof, in unit dosage form, together with instructions for administering the compound to a subject suffering from or susceptible to a brain tumor. In any of the embodiments presented herein, the brain tumor is a brain cancer. In any of the embodiments presented herein, the brain tumor is of brain tissue origin. In any of the embodiments presented herein, the brain tumor is not of brain tissue origin (i.e., tumors that originate outside of the brain and metastasize to the brain). In any of the embodiments presented herein, the brain tumor is of lung, breast, skin (e.g., melanoma), colon, or kidney tissue origin. In any of the embodiments presented herein, the brain tumor is androgen positive. In any of the embodiments presented herein, the brain tumor is CYP17 positive. In any of the embodiments presented herein, the brain tumor is androgen positive and CYP17 positive. In another aspect, the brain cancer is androgen receptor positive. In any of the embodiments presented herein, the brain cancer is CYP17 positive. In any of the embodiments presented herein, the brain cancer is androgen positive and CYP17 positive. In another aspect, the brain cancer is a glioma, a meningioma, or a medulloblastoma. In another aspect, the brain cancer is a glioma. In another aspect, the glioma is a glioblastoma, an astrocytoma, an oligodendroglioma, or an ependyoma. In another aspect, the glioma is glioblastoma multiforme (GBM).

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebroventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *Theobroma*; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *Echinacea*, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also be used in the pharmaceutical compositions herein.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the presently disclosed subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197, 934; 6,056,950; 5,800,807; 5,776,445; 5,698,219; 5,521, 222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407, 713; 5,352,456; 5,332,213; 5,336,168; 5,290,561; 5,254, 346; 5,164,189; 5,163,899; 5,088,977; 5,087,240; 5,008, 110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment includes that embodiment as any single embodiment or in combination with any other embodiments or portions thereof.

EXAMPLES

The present invention will now be demonstrated using specific examples that are not to be construed as limiting.

General Experimental Procedures

Definitions of variables in the structures in schemes herein are commensurate with those of corresponding positions in the formulae delineated herein.

Synthesis of 4-(1,2,3-Triazoles)

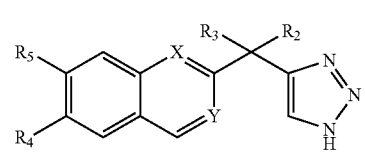

Syntheses of 4-substituted 1,2,3-triazole targets (III) may be accomplished using the example synthesis that is shown below (e.g, Scheme A, Scheme 1). A broad range of R4 and R5-substituted naphthalenes may be prepared starting from functionalized halo- and alkoxy-naphthalene starting materials (e.g. A). The A may be prepared by Friedel-Crafts acylation of 2,3-dimethoxy-naphthalene with isobutyryl chloride/aluminum trichloride. Addition of lithiated 1-N-(2-(trimethylsilylethoxymethyl-1,2,3,-triazole to ketone A affords a tertiary alcohol intermediate that can be de-protected with a fluoride source (e.g. cesium fluoride) to afford 1. For compounds III wherein R4 or R5 are aryl or heteroaryl, these groups may be added to Br-naphthalene intermediates (R4 or R5=Br) via Suzuki coupling methodology [aryl-B(OH)2 or heteroaryl-B(OH)2, palladium (II) acetate catalysis].

In embodiments, the invention provides for the intermediate compounds of the formulae delineated herein and methods of converting such compounds to compounds of the formulae herein (e.g., in Scheme A, A1 to A2; A2 to A3; A1 to A3) comprising reacting a compound herein with one or more reagents in one or more chemical transformations (including those provided herein) to thereby provide the compound of any of the formulae herein or an intermediate compound thereof.

The synthetic methods described herein may also additionally include steps, either before or after any of the steps described in any scheme, to add or remove suitable protecting groups in order to ultimately allow synthesis of the compound of the formulae described herein. The methods delineated herein contemplate converting compounds of one formula to compounds of another formula (e.g., in Scheme A, A1 to A2; A2 to A3; A1 to A3). The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, sublimation, crystallization, trituration, solid phase extraction, and chromatography).

Scheme A

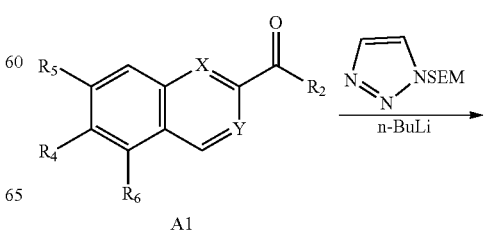

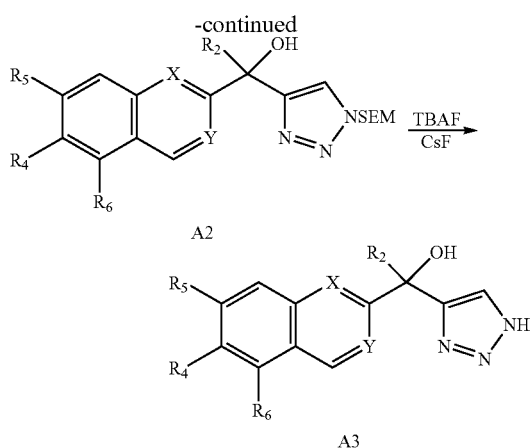

A2

A3

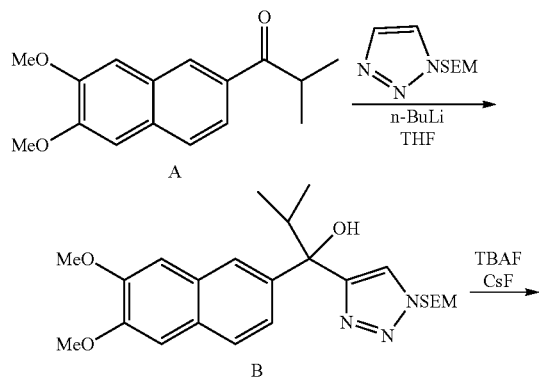

Scheme 1

A

B

1

Example 1

1-(6,7-Dimethoxynaphthalen-2-yl)-2-methyl-1-(1H-1,2,3-triazol-4-yl)propan-1-ol (1)

To a stirred solution of N-2-(trimethylsilyl)ethoxymethyl-1,2,3-triazole (0.25 g, 1.2 mmol) in dry THF (7 mL) was added n-BuLi (0.86 mL, 1.38 mmol, 1.6M solution) at −78° C. After being stirred for 1 h at −78° C., compound A (0.421 g, 1.63 mmol) in THF (7 mL) was added at −78° C., and the reaction was allowed to warm to RT and stirred for 16 h. The reaction mixture was quenched with saturated NH₄Cl solution and extracted with ethyl acetate (2×25 mL). Combined organic phases were washed with brine, dried over anhydrous Na₂SO₄ and concentrated under reduced pressure to afford B (0.25 g) as a syrup. The crude material was taken up for next step without further purification.

Preparation of N-2-(trimethylsilyl)ethoxymethyl-1,2,3-triazole

To a stirred solution of 1,2,3-triazole (2.0 g, 28.9 mmol) in THF (10 mL) was added NaH (1.065 g, 43.1 mmol) portion wise at 0° C. under inert atmosphere. After being stirred for 45 min at 0° C., 2-(trimethylsilyl)ethoxymethyl-Cl (SEM-Cl; 7.6 mL, 43.1 mmol) was added to the reaction mixture. After completion of addition the reaction mixture was allowed to warm to RT and stirred for 12 h. The reaction mixture was quenched with water and extracted with ethyl acetate (2×100 mL). The combined organic extracts were washed with brine, dried over anhydrous Na₂SO₄ and concentrated under reduced pressure to give crude compound. The crude material was purified by column chromatography eluting with 10% EtOAc/hexane to afford N-2-(trimethylsilyl)ethoxymethyl-1,2,3-triazole (3.5 g, 17.5 mmol, 61%) as a liquid.

Mass: m/z 200 [M⁺+1].

To a stirred solution of B (0.15 g, 0.32 mmol) in THF (30 mL) was added TBAF (1.5 mL, 1 M in THF) and the reaction mixture was heated at reflux temperature for 3 h. The reaction mixture was concentrated in vacuo; the obtained residue was partitioned between water and DCM. The organic phase was separated and aqueous layer was extracted with DCM (2×25 mL); the combined organic phases were washed with brine, dried over anhydrous Na₂SO₄, and concentrated under reduced pressure to give crude material. The crude material was purified by column chromatography (SiO₂, 100-200 mesh) to afford 1 (25 mg, 0.07 mmol, 25%) as a white solid. ¹H NMR (500 MHz, CDCl₃): δ 11.4 (br s, 1H), 7.88 (s, 1H), 7.72 (s, 1H), 7.65 (d, J=8.5 Hz, 1H), 7.49 (d, J=8.0 Hz, 1H), 7.12 (s, 1H), 7.09 (s, 1H), 3.98 (s, 6H), 2.81 (m, 1H), 0.96 (d, J=6.5 Hz, 3H), 0.83 (d, J=6.5 Hz, 3H). HPLC: 98.6%. MS (ESI): m/z 326 398 [M+H]⁺.

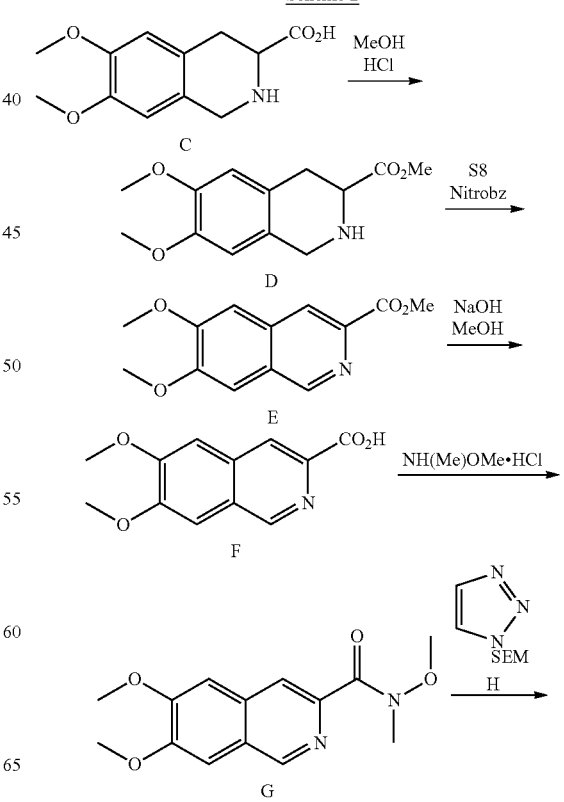

Scheme 2

C

D

E

F

G

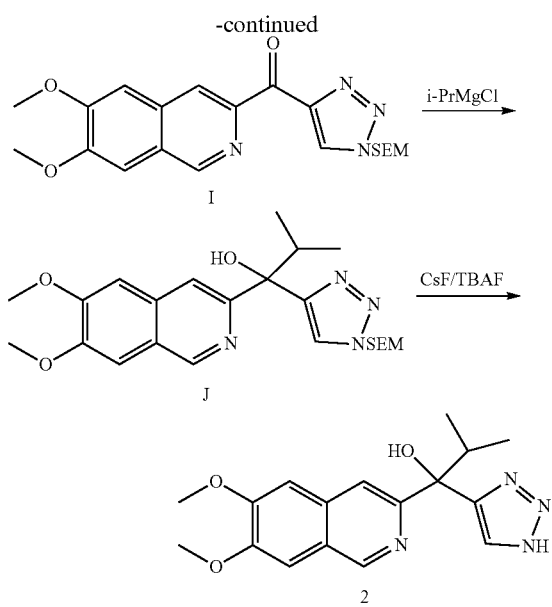

Example 2

1-(6,7-Dimethoxyisoquinolin-3-yl)-2-methyl-1-(1H-1,2,3-triazol-4-yl)propan-1-ol (2)

A solution of C (1.0 g, 4.2 mmol in sat'd methanolic HCl (120 mL) was stirred at reflux for 50 h. After the consumption of starting material (by TLC), the volatiles were evaporated under reduced pressure. The resulting residue was dissolved in ice-cold water and basified to pH~ 10 using saturated aq. $K_2CO_3$ solution, and then extracted with $CHCl_3$ (6×50 mL). The combined organic layers were washed with brine, dried over anhydrous $Na_2SO_4$, and concentrated under reduced pressure to afford ester D (0.85 g, 3.38 mmol, 85%) as a white solid. $^1$H NMR (500 MHz, $CDCl_3$): δ 6.59 (s, 1H), 6.52 (s, 1H), 4.06-3.98 (m, 2H), 3.83 (s, 6H), 3.78 (s, 3H), 3.73-3.71 (m, 1H), 2.99 (dd, J=4.5, 16 Hz, 1H), 2.89 (dd, J=8.5, 16 Hz, 1H). Mass: m/z 252 [M$^+$+1].

To a stirred solution of ester D (0.65 g, 2.58 mmol) in nitrobenzene (30 mL) was added S8 (0.20 g, 6.47 mmol) at RT under inert atmosphere. The reaction mixture was stirred at 140° C. for 14 h. After consumption of starting material, the nitrobenzene was evaporated under reduced pressure. The resulting residue was dissolved in cold 1 N HCl solution and washed twice with toluene. The aqueous layer was basified to pH~ 10 using saturated $K_2CO_3$ solution and extracted with ethyl acetate (3×50 mL). The combined organic layers were washed with brine, dried over anhydrous $Na_2SO_4$, and concentrated under reduced pressure to afford E (0.43 g, 1.74 mmol, 67.2%) as an off white solid. $^1$H NMR (500 MHz, $CDCl_3$): δ 9.12 (s, 1H), 8.47 (s, 1H), 7.29 (s, 1H), 7.20 (s, 1H), 4.07-4.03 (m, 9H). Mass: m/z 248 [M$^+$+1].

To a stirred solution of E (0.20 g, 0.809 mmol) in MeOH (5 mL) was added a solution of NaOH (0.097 g, 2.42 mmol) in $H_2O$ (1 mL) at 0° C. The reaction mixture was allowed to warm to RT and was stirred for 12 h. The volatiles were removed under reduced pressure. The obtained residue was dissolved in water, acidified with 1 N HCl, and stirred for 15 min at 0° C. The precipitate was filtered and dried under vacuum to afford acid F (0.13 g, 0.55 mmol, 69%) as white solid. $^1$H NMR (500 MHz, DMSO-$d_6$): δ 9.10 (s, 1H), 8.41 (s, 1H), 7.59 (s, 1H), 7.55 (s, 1H), 3.94 (s, 6H).

To a stirred solution of acid F (2.0 g, 8.58 mmol) in DMF (10 mL) were added EDCI (2.46 g, 12.8 mmol), HOBT (1.15 g, 8.58 mmol), NMM (3.7 mL, 34.3 mmol), and N,O-dimethylhydroxylamine hydrochloride (1.25 g, 12.8 mmol) at 0° C. under inert atmosphere. After completion of addition the reaction mixture was allowed to warm to RT and stirred for 5 h. The reaction mixture was quenched with ice-cold water and extracted with ethyl acetate (2×100 mL). The combined organic extracts were washed with brine, dried over anhydrous $Na_2SO_4$, and concentrated under reduced pressure to obtain the crude product. The crude material was purified by column chromatography eluting with EtOAc/hexane to afford Weinreb amide G (1.6 g, 5.79 mmol, 70%) as syrup. $^1$H NMR (500 MHz, $CDCl_3$): δ 9.02 (s, 1H), 8.02 (s, 1H), 7.24 (s, 1H), 7.14 (s, 1H), 4.05 (s, 6H), 3.81 (s, 3H), 3.47 (s, 3H).

Mass: m/z 277 [M$^+$+1].

To a stirred solution of H (0.43 g, 2.17 mmol) in ether (10 mL) was added t-BuLi (2.13 mL, 3.6 mmol) dropwise at −70° C. under inert atmosphere. After stirring for 1 h at −70° C., Weinreb amide-G (0.20 g, 0.72 mmol) in THF (5 mL) was added to the reaction mixture. After stirring for an additional 30 min at −70° C., the reaction mixture was quenched with water and extracted with ethyl acetate (3×50 mL). Combined organic phases were washed with brine, dried over anhydrous $Na_2SO_4$, and concentrated under reduced pressure to give crude material. The crude material was purified by column chromatography to afford ketone I (0.11 g, 0.27 mmol, 38.3%) as syrup. $^1$H NMR (500 MHz, $CDCl_3$): δ 9.18 (s, 1H), 9.12 (s, 1H), 8.57 (s, 1H), 7.83-7.78 (m, 1H), 7.37 (s, 1H), 5.77 (s, 2H), 4.15 (s, 3H), 4.14 (s, 3H), 3.74-3.66 (m, 2H), 1.00-0.94 (m, 2H), 0.0-0.00 (m, 9H). Mass: m/z 415 [M$^+$+1].

To a stirred solution of ketone I (0.12 g, 0.28 mmol) in THF (3 mL) was added isopropyl magnesium chloride (0.72 mL, 1.44 mmol) dropwise at 0° C. under inert atmosphere. After stirring for 1 h at RT, the reaction mixture was quenched with water and extracted with ethyl acetate (3×50 mL). The combined organic extracts were washed with brine, dried over anhydrous $Na_2SO_4$, and concentrated under reduced pressure to afford alcohol J (55 mg, 0.12 mmol, 74%) as syrup. 1H NMR of the crude material showed all the required peaks along with some impurities. The crude product was taken ahead to the next step without further purification. Mass: m/z 459 [M$^+$+1].

To a stirred solution of alcohol J (0.24 g, 0.52 mmol) in THF (5 mL) were added TBAF (0.05 mL, 0.052 mmol, 1 M in THF) and CsF (0.15 g, 1.04 mmol) at RT under inert atmosphere. The reaction mixture was stirred at reflux temperature for 12 h. The volatiles were evaporated under reduced pressure to give crude compound. The crude material was purified by column chromatography eluting with 30% EtOAc/hexane to afford 2 (90 mg, 0.27 mmol, 52%) as a white solid. $^1$H NMR (500 MHz, $CDCl_3$): δ 8.87 (s, 1H), 7.88-7.81 (m, 2H), 7.18 (s, 1H), 7.09 (s, 1H), 4.01 (s, 6H), 2.74-2.66 (m, 1H), 0.97 (d, J=6.6 Hz, 3H), 0.71 (d, J=6.6 Hz, 3H). HPLC: 93.55%. Mass: m/z 329 [M$^+$+1].

(+)-Enantiomer of (2)
Chiral Preparative HPLC Specifications:
Column: Chiralpak IC, 250×4.6 mm, 5-micron
Mobile Phase: A) n-Hexane, B) IPA
Isocratic: A: B (95:5)
Flow rate: 1.00 mL/min
HPLC: 99.2% (11 mg isolated as a white powder).
Optical rotation $[α]_D$: +7.6° (c=0.5% in MeOH).

(−)-Enantiomer of (2)
Chiral Preparative HPLC Specifications:
Column: Chiralpak IC, 250×4.6 mm, 5-micron
Mobile Phase: A) n-Hexane, B) IPA
Isocratic: A: B (95:5)
Flow rate: 1.00 mL/min
HPLC: 99.8% (12 mg isolated as a white powder).
Optical rotation $[\alpha]_D$: −5.8° (c=0.5% in MeOH).

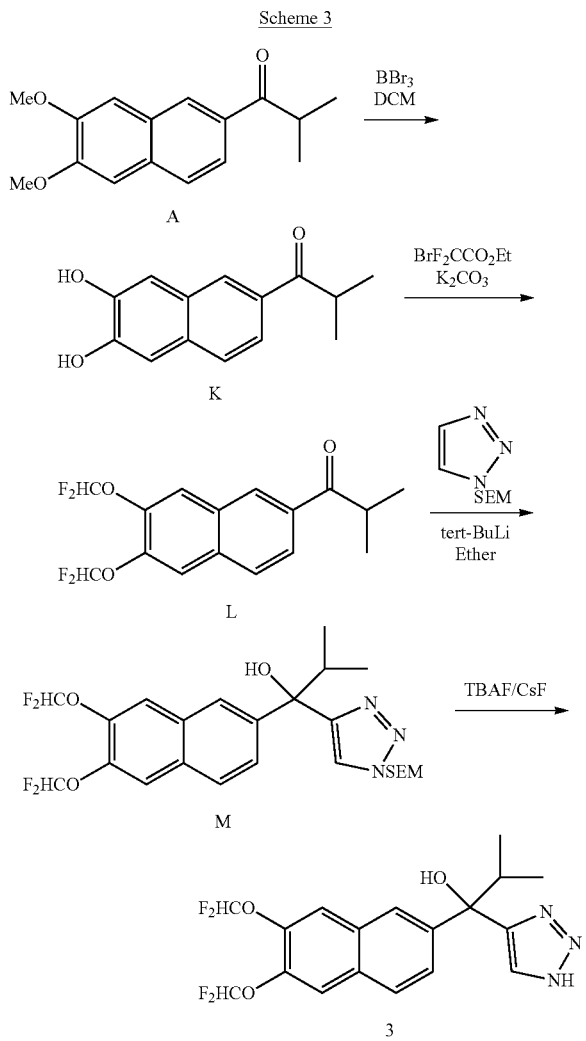

Example 3

Figure 5:
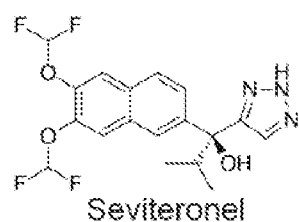
FIG. 5. depicts the structure of seviteronel.
Figure 6A:
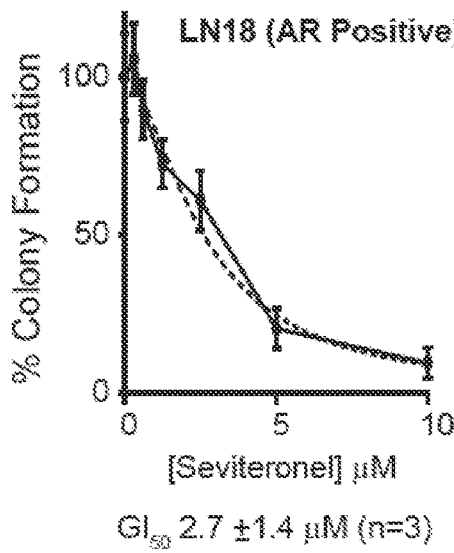
FIG. 6A to 6D depict the dose-dependent inhibition of AR positive GBM tumor cell lines by seviteronel.
Figure 6B:
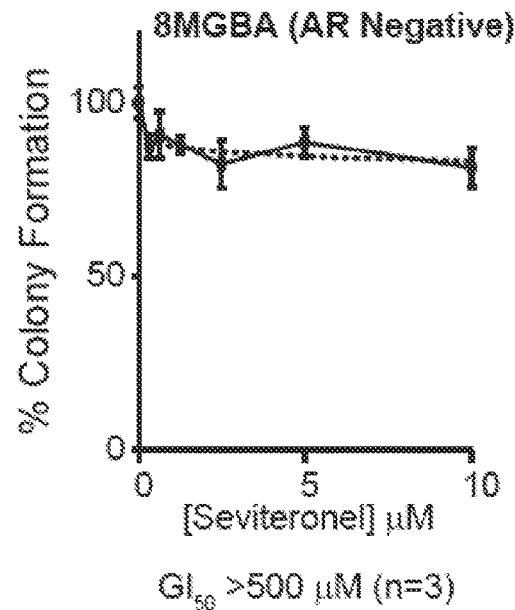
Figure 6C:
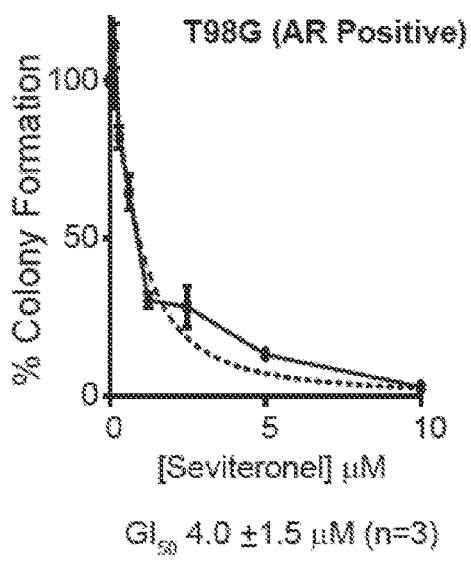
Figure 6D:
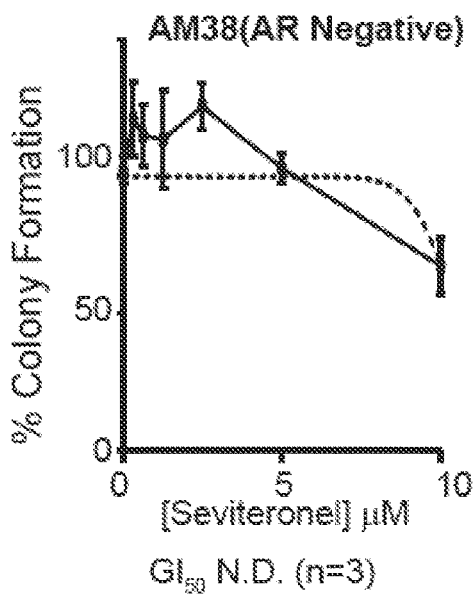
Figure 7A:
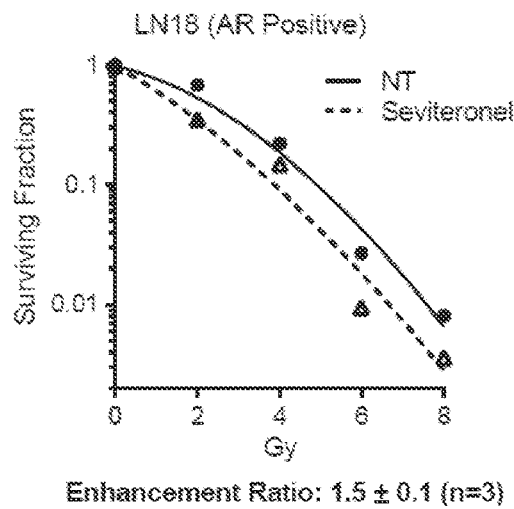
FIG. 7A to 7D depict the relation between radiation dose (Gy) and surviving fraction of cells in different AR positive cell lines and AR negative cell lines in the presence or absence of seviteronel, where 2.5 µM of seviteronel was administered for LN18 and 5 µM of seviteronel was administered for T98G.
Figure 7B:
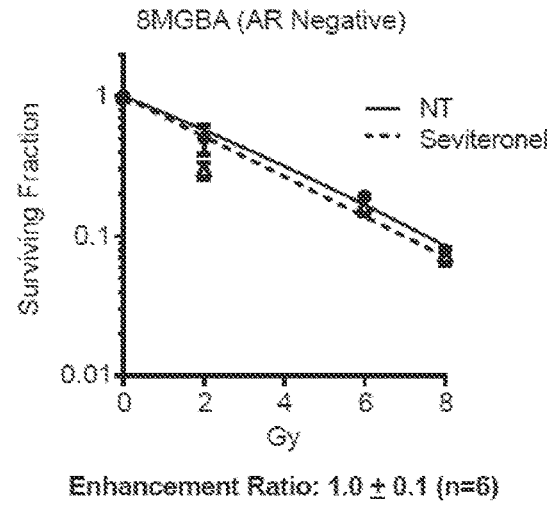
Figure 7C:
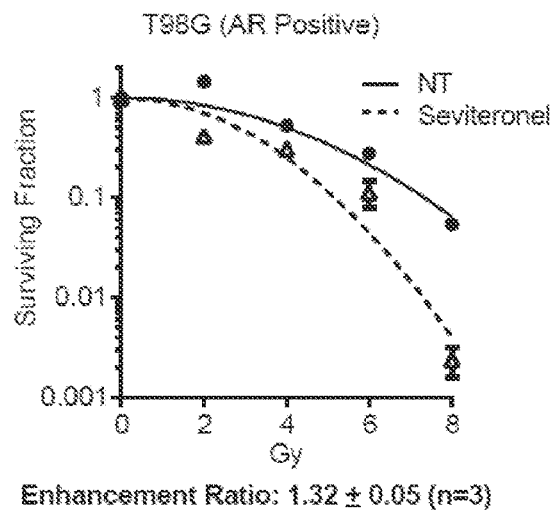
Figure 7D:
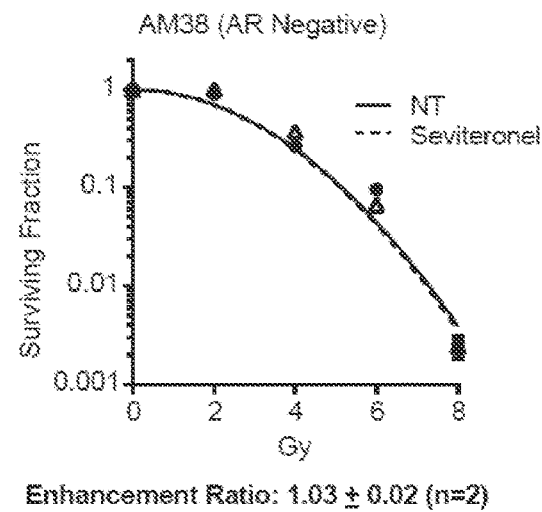

1-(6,7-Bis(difluoromethoxy)naphthalen-2-yl)-2-methyl-1-(1H-1,2,3-triazol-4-yl)propan-1-ol (3)
(FIG. 5)

To a stirred solution of A (18 g, 69 mmol) in DCM (180 mL) was added BBr$_3$ (87.2 g, 348 mmol) dropwise at −40° C. After completion of addition, stirring was continued for 1 h at −40° C. and 1 h at RT. The reaction mixture was poured into cold water and aqueous layer was then extracted with DCM (2×200 mL). The combined organic extracts were washed with water (100 mL), brine (100 mL) and dried over anhydrous Na$_2$SO$_4$. After filtration and evaporation of solvent under reduced pressure, the crude material was purified by column chromatography (SiO$_2$, 100-200 mesh) to afford K (9.0 g, 39 mmol, 56%) as a brown solid. $^1$H NMR (200 MHz, CDCl3): δ☐ 8.29 (s, 1H), 7.88 (dd, J=8.8, 1.6 Hz, 1H), 7.68 (d, J=8.6 Hz, 1H), 7.36 (s, 1H), 7.26 (s, 1H), 5.88 (br s, 2H), 3.79-3.63 (m, 1H), 1.27 (d, J=6.8 Hz, 6H).

To a stirred solution of K (5.0 g, 21.7 mmol) in DMF (50 mL) were added ethyl bromo difluoroacetate (17.6 g, 86.6 mmol) and K$_2$CO$_3$ (18 g, 130 mmol) and the mixture was stirred at 110° C. for 48 h. The reaction mixture was poured into cold water and aqueous layer was then extracted with DCM (2×100 mL). Combined organic extracts were washed with water (50 mL), brine (50 mL), and dried over anhydrous Na$_2$SO$_4$. After filtration and evaporation of solvent under reduced pressure, the crude material was purified by column chromatography (SiO$_2$, 100-200 mesh) to afford L (2.3 g, 4.3 mmol, 32%) as a solid. $^1$H NMR (500 MHz, CDCl3): δ☐ 8.40 (s, 1H), 8.05 (dd, J=8.5, 1.5 Hz, 1H), 7.86 (d, J=9.0 Hz, 1H), 7.79 (s, 1H), 7.68 (s, 1H), 6.67 (t, $J_{F,H}$=73 Hz, 1H), 6.65 (t, $J_{F,H}$=73 Hz, 1H), 3.72-3.65 (m, 1H), 1.27 (d, J=7.0 Hz, 6H).

To a stirred solution of N-SEM-1,2,3-triazole (2.25 g, 11.8 mmol) in dry ether (25 mL) was added t-BuLi (0.69 g, 10.7 mmol) dropwise at −78° C. under inert atmosphere. After stirring for 1 h at −78° C., compound-L (1.5 g, 2.83 mmol) in dry ether (25 mL) was added to reaction mixture and stirring was continued for additional 1 h at −78° C. The reaction mixture was quenched with saturated NH$_4$Cl solution and extracted with ethyl acetate (2×50 mL). Combined organic phases were washed with brine, dried over anhydrous Na$_2$SO$_4$ and concentrated under reduced pressure to afford M (2.0 g) as thick syrup. Crude material was taken up for next step without further purification.

To a stirred solution of M (3.0 g, 5.6 mmol) in THF (30 mL) were added TBAF (1.48 g, 5.67 mmol, 1 M in THF) and CsF (2.58 g, 16.8 mmol) at RT under inert atmosphere. The reaction mixture was stirred at 80° C. for 4 h. The mixture was concentrated in vacuo; the obtained residue was partitioned between water and DCM. The organic phase was separated and the aqueous layer was extracted with DCM (2×25 mL); the combined organic phases were washed with brine, dried over anhydrous Na$_2$SO$_4$, and concentrated under reduced pressure to give crude material. The crude material was purified by column chromatography (SiO$_2$, 100-200 mesh) to afford 3 (2.2 g, 5.5 mmol, 61%) as a white solid. $^1$H NMR (500 MHz, CDCl$_3$): δ☐ 11.4 (br, 1H), 8.03 (s, 1H), 7.76-7.61 (m, 5H), 6.60 (t, $J_{F,H}$=74 Hz, 2H). 2.88 (br s, 1H), 2.86-2.80 (m, 1H), 0.97 (d, J=7.0 Hz, 3H), 0.80 (d, J=7.0 Hz, 3H). HPLC: 96%. MS (ESI): m/z 398 [M+H]$^+$.

(+)-Enantiomer of (3)
Chiral Preparative HPLC Specifications:
Column: Chiralpak IC, 250×4.6 mm, 5-micron
Mobile Phase: A) n-Hexane, B) IPA
Isocratic: A: B (95:5)
Flow rate: 1.00 mL/min
HPLC: 98.1% (15 mg isolated as a white powder).
Optical rotation $[\alpha]_D$: +41.5° (c=0.5% in MeOH).

(−)-Enantiomer of (3)
Chiral Preparative HPLC Specifications:
Column: Chiralpak IC, 250×4.6 mm, 5-micron
Mobile Phase: A) n-Hexane, B) IPA
Isocratic: A: B (95:5)
Flow rate: 1.00 mL/min
HPLC: 99.5% (13 mg isolated as a white powder).
Optical rotation $[\alpha]_D$: −54° (c=0.5% in MeOH).

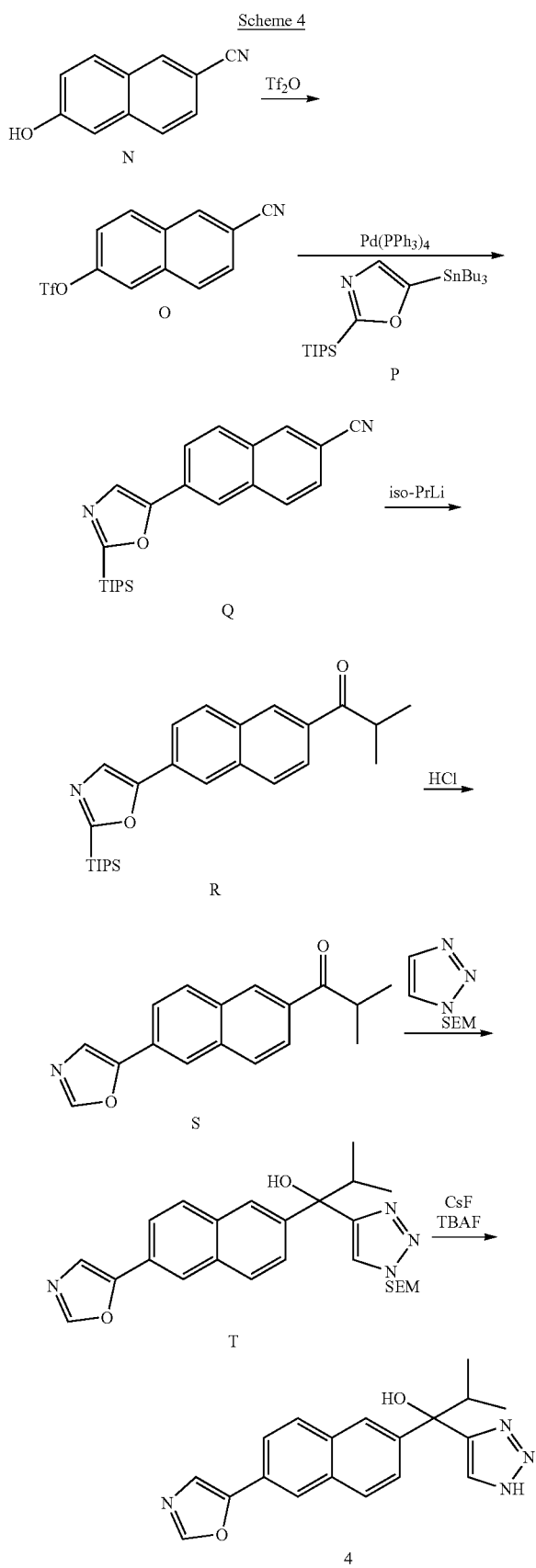

Example 4

2-Methyl-1-(6-(oxazol-5-yl)naphthalen-2-yl)-1-(1H-1,2,3-triazol-4-yl)propan-1-ol (4)

To a stirred solution of 6-hydroxy-2-naphthonitrile N (3.0 g, 17.7 mmol) in DCM (90 mL) were added triethylamine (2.68 g, 26.5 mmol) and triflic anhydride (7.5 g, 26.5 mmol) at 0° C. and stirring was continued for an additional 1 h at 0° C. The reaction mixture was partitioned between water and DCM; the organic phase was separated, dried over anhydrous $Na_2SO_4$, and concentrated under reduced pressure to give crude material. The crude material was purified by column chromatography ($SiO_2$, 100-200 mesh) eluting with 3% EtOAc/hexane to afford alcohol O (4.2 g, 13.9 mmol, 78%) as a solid. $^1$H NMR (200 MHz, $CDCl_3$): δ 8.30 (s, 1H), 8.00 (app t, 2H), 7.83 (d, J=2.6 Hz, 1H), 7.74 (dd, J=8.8, 1.8 Hz, 1H), 7.51 (dd, J=8.8, 2.2 Hz, 1H).

Preparation of 5-(Tributylstannyl)-2-(triisopropylsilyl)oxazole (P)

To a stirred solution of oxazole (3.0 g, 43.4 mmol) in diethyl ether (90 mL) was added n-BuLi (28 mL, 47.8 mmol, 1.6 M in hexane) dropwise at −78° C. under inert atmosphere. After stirring for an additional 45 min at −78° C., triisopropyl trifluoromethane sulfonate (11.1 mL, 43.4 mmol) was added slowly to reaction mixture at −78° C. After completion of addition, the reaction mixture was slowly allowed to warm to RT and was stirred for 12 h. The mixture was quenched with n-hexane and volatiles were evaporated under reduced pressure. The obtained crude material was purified by column chromatography to afford 2-TIPS-oxazole (8.0 g, 35.5 mmol, 81%) as a syrup.

$^1$H NMR (500 MHz, $CDCl_3$): δ 7.81 (s, 1H), 7.20 (s, 1H), 1.45-1.37 (m, 3H), 1.80-1.56 (m, 18H). MS (ESI): m/z 226 [M+H]$^+$. To a stirred solution of 2-TIPS-oxazole (2.5 g, 11.1 mmol) in diethyl ether (50 mL) was added tert-BuLi (10.4 mL, 17.0 mmol, 1.6 M in hexane) dropwise at −78° C. under inert atmosphere. After stirring for additional 1 h at −78° C., tri-n-butyl stannyl chloride (5.7 g, 17.0 mmol) was added slowly to reaction mixture at −78° C. After completion of addition reaction mixture was slowly allowed to warm to RT and stirred for 1 h. The reaction mixture was quenched with water and extracted with EtOAc. The organic phase was washed with brine, dried over anhydrous $Na_2SO_4$ and concentrated under reduced pressure to afford P (5.0 g, 9.7 mmol, 87%) as a syrup. MS (ESI): m/z 516 [M+H]$^+$.

Compound O (2.5 g, 8.27 mmol) was dissolved in 1,4-dioxane (100 mL) and the mixture was purged with argon for a period of 20 min. Pd(PPh$_3$)$_4$ (0.152 g, 0.20 mmol) was added followed by compound P (6.3 g, 12.4 mmol) in 1,4-dioxane (20 mL) under an inert atmosphere. The reaction mixture was stirred for 2 h at 120° C. The reaction was evaporated in vacuo and the obtained crude material was purified by column chromatography ($SiO_2$, 100-200 mesh) to afford Q (1.5 g, 3.9 mmol, 48%) as a solid. $^1$H NMR (200 MHz, $CDCl_3$): δ 8.22 (s, 1H), 8.14 (s, 1H), 7.99-7.87 (m, 3H), 7.67-7.61 (m, 2H), 1.58-1.42 (m, 3H), 1.25-1.19 (m, 18H). MS (ESI): m/z 377 [M+H]$^+$.

To a stirred solution of Q (1.5 g, 3.98 mmol) in anhydrous diethyl ether (60 mL) was added i-PrLi (14.1 mL, 9.9 mmol, 0.7 M in diethyl ether) drop wise at −78° C. under inert atmosphere and the mixture was stirred for additional 1 h at −78° C. The reaction mixture was quenched with saturated $NH_4Cl$ and stirred for 1 h. The organic phase was separated and aqueous phase was extracted with diethyl ether. The combined organic phases were washed with brine, dried over anhydrous Na₂SO₄, and concentrated under reduced pressure to obtain crude compound. The crude material was purified by column chromatography to afford R (1.1 g, 2.6 mmol, 65%) as a solid.

¹H NMR (200 MHz, CDCl₃): $\epsilon$☐ 8.45 (s, 1H), 8.14 (s, 1H), 8.09-7.93 (m, 3H), 7.80 (dd, J=8.4, 1.6 Hz, 1H), 7.59 (s, 1H), 3.80-3.69 (m, 1H), 1.54-1.39 (m, 3H), 1.31-1.20 (m, 24H).

MS (ESI): m/z 421.9 [M+H]⁺.

To a stirred solution of R (1.1 g, 2.61 mmol) in THF (21 mL) was added 2 N HCl (11 mL) at 0° C. and the reaction mixture was stirred for 30 min at RT. The reaction mixture was basified with saturated NaHCO₃ solution and extracted with EtOAc (2×50 mL). The combined organic layers were washed with water and brine, dried over anhydrous Na₂SO₄, and concentrated under reduced pressure to obtain crude compound. The crude material was purified by column chromatography (SiO₂, 100-200 mesh) eluting with 20% EtOAc/hexane to afford S (0.6 g, 2.26 mmol, 87%) as a white solid. ¹H NMR (200 MHz, CDCl₃): δ☐ 8.46 (s, 1H), 8.17 (s, 1H), 8.10-7.92 (m, 4H), 7.80 (dd, J=8.6, 1.8 Hz, 1H), 7.54 (s, 1H), 3.79-3.66 (m, 1H), 1.30 (d, J=6.8. Hz, 6H). MS (ESI): m/z 266 [M+H]⁺.

To a stirred solution of N-1-SEM-1,2,3-triazole (H, 0.45 g, 2.26 mmol) in dry ether (6 mL) was added t-BuLi (1.3 mL, 2.26 mmol) drop wise at −78° C. under inert atmosphere. After stirring for 1 h at −78° C., compound-S (0.17 g, 0.63 mmol) in THF (5 mL) was added to reaction mixture and stirring was continued for additional 2 h at RT. The reaction mixture was quenched with saturated NH₄Cl solution and extracted with ethyl acetate (2×50 mL). Combined organic phases were washed with brine, dried over anhydrous Na₂SO₄, and concentrated under reduced pressure to afford T (0.26 g) as a syrup. The crude material was taken up for next step without further purification.

To a stirred solution of T (0.2 g, 0.43 mmol) in THF (4 mL) were added TBAF (0.21 mL, 1 M in THF) and CsF (0.09 g, 1.29 mmol) at RT under inert atmosphere. The reaction mixture was stirred at 80° C. for 4 h. The reaction mixture was concentrated in vacuo; the obtained residue was dissolved in water. The aqueous layer was extracted with EtOAc (2×50 mL); the combined organic phases were washed with brine, dried over anhydrous Na₂SO₄, and concentrated under reduced pressure to give crude material. The crude material was purified by column chromatography (SiO₂, 100-200 mesh) eluting with 15% EtOAc/hexane to afford 4 (35 mg, 0.10 mmol, 24%) as a solid. ¹H NMR (500 MHz, CDCl₃): δ☐ 8.47 (s, 1H), 8.17 (s, 1H), 8.06 (s, 1H), 7.96 (d, J=8.5 Hz, 1H), 7.88 (d, J=8.5 Hz, 1H), 7.81 (d, J=8.5 Hz, 1H), 7.78 (s, 1H), 7.75-7.67 (m, 2H), 5.70 (s, 1H), 2.74 (m, 1H), 0.83 (d, J=7.0. Hz, 3H), 0.67 (d, J=7.0. Hz, 3H). HPLC: 97%. MS (ESI): m/z 335 [M+H]⁺.

Scheme 5

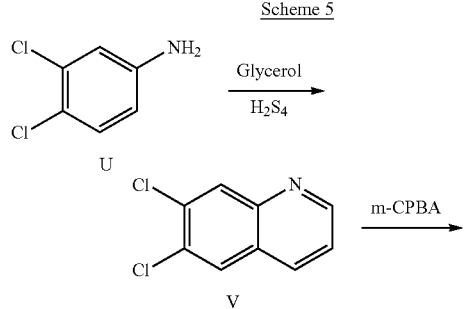

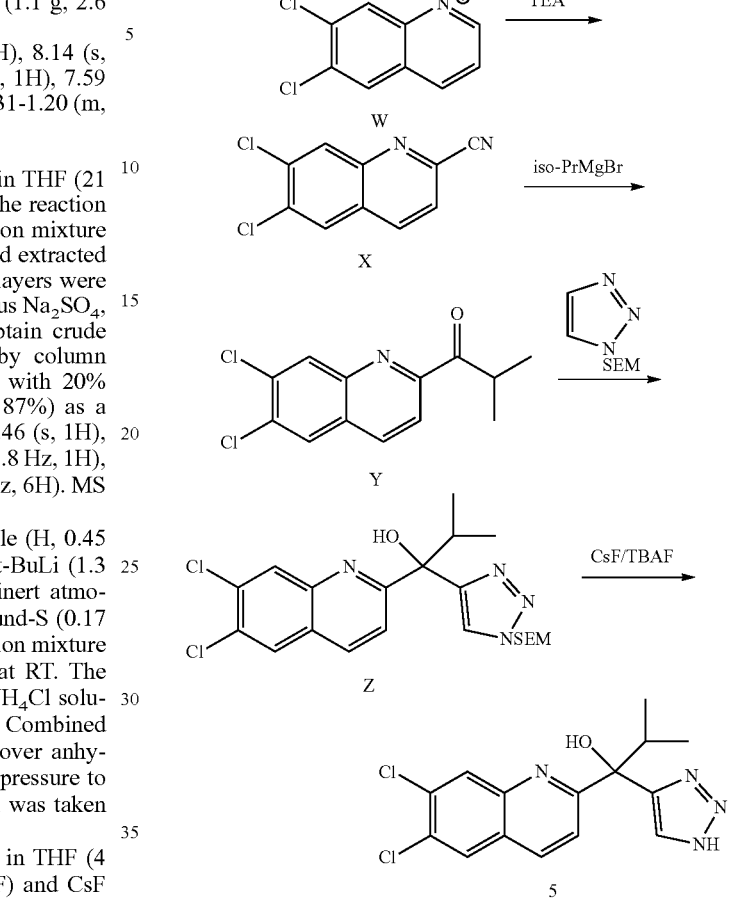

Example 5

1-(6,7-Dichloroquinolin-2-yl)-2-methyl-1-(1H-1,2,3-triazol-4-yl)propan-1-ol (5)

To a mixture of sodium 3-nitrobenzenesulfonate (90 g, 401.2 mmol) in conc. H₂SO₄ (50 mL) and H₂O (30 mL) was added glycerol (18.7 g, 203.2 mmol) and the mixture was stirred for 10 min at 150° C. 3,4-Dichloroaniline U (10.0 g, 61.7 mmol) was then added to the reaction mixture and stirring was continued for 12 h at 150° C. The pH of the reaction mixture was adjusted to ~9 with 50% aq. NaOH solution at 0° C. and extracted with EtOAc (2×250 mL). The combined organic phases were washed with water (100 mL) and brine (100 mL), dried over anhydrous Na₂SO₄, filtered, and concentrated in vacuo. The crude material was purified by recrystallization using ethanol to afford V (mixture of 5,6- and 6,7-regioisomers) (8 g, 40 mmol, 65%) as a solid.

To a stirred solution of V (mixture of 5,6- and 6,7-regio isomers) (10.0 g, 50.5 mmol) in EtOAc (200 mL) was added m-CPBA (17.4 g, 101 mmol) and the reaction mixture was stirred at RT for 6 h. The precipitated solid was filtered and dried in vacuo to afford W (mixture of 5,6- and 6,7-regio isomers) (2.3 g, 10.7 mmol, 21%) as a solid.

To a stirred solution of W (mixture of 5,6- and 6,7-regio isomers) (2.3 g, 10.7 mmol) in MeCN (40 mL) was added TEA (5.8 mL, 7.63 mmol), followed by TMSCN (5.7 mL, 37.6 mmol), at RT under an inert atmosphere. The reaction mixture was stirred at RT for 12 h. The volatiles were evaporated under reduced pressure and the crude material was purified by column chromatography (SiO$_2$, 60-120 mesh) to afford X as a mixture of 5,6- and 6,7-regio isomers (2.0 g, 9.0 mmol, 80%). After recrystallization of the solid from hot MeCN, the 5,6-regioisomer was precipitated and collected by filtration. The filtrate was concentrated in vacuo to afford pure X (6,7-regioisomer) (1 g, 4.5 mmol, 40%) as a solid. $^1$H NMR (200 MHz, CDCl$_3$): δ☐ 8.31 (s, 1H), 8.24 (d, J=8.6 Hz, 1H), 8.03 (s, 1H), 7.71 (d, J=8.4 Hz, 1H).

To a stirred solution of X (1.0 g, 4.5 mmol) in toluene (60 mL) was added a catalytic amount of CuBr (0.06 g, 0.45 mmol) at RT under N$_2$ atmosphere. The reaction mixture was cooled to 0° C.; isopropylmagnesium bromide (11.2 mL, 11.2 mmol, 1 M in diethyl ether) was then added to the reaction mixture dropwise and stirring continued for another 20 min at 0° C. The reaction mixture was quenched with cold water and filtered through Celite. The filtrate was extracted with ethyl acetate (2×50 mL); the combined organic extracts were washed with brine, dried over anhydrous Na$_2$SO$_4$, and concentrated under reduced pressure to afford Y (0.6 g, 2.24 mmol, 50%) as a solid. $^1$H NMR (500 MHz, CDCl$_3$): δ☐ 8.33 (s, 1H), 8.18 (d, J=9.0 Hz, 1H), 8.13 (d, J=8.0 Hz, 1H), 7.99 (s, 1H), 4.32-4.26 (m, 1H), 1.26 (d, J=7.0 Hz, 6H).

To a stirred solution of N-1-SEM-1,2,3-triazole (H, 0.76 g, 3.82 mmol) in dry diethyl ether (6 mL) was added t-BuLi (1.7 M in pentane, 2.2 mL, 3.82 mmol) dropwise at −70° C. under inert atmosphere. After stirring for 1 h at −70° C., a solution of compound Y (0.17 g, 0.63 mmol) in diethyl ether (5 mL) was added to the reaction mixture and stirring was continued for an additional 1 h at −70° C. The reaction mixture was quenched with saturated NH$_4$Cl solution and extracted with ethyl acetate (2×50 mL). The combined organic phases were washed with brine, dried over anhydrous Na$_2$SO$_4$ and concentrated under reduced pressure to afford Z (0.18 g) as a solid. The crude material was taken up for next step without further purification. MS (ESI): m/z 466 [M+H]$^+$.

To a stirred solution of Z (0.4 g, 0.85 mmol) in THF (10 mL) were added TBAF (0.4 mL, 1 M in THF) and CsF (0.38 g, 2.57 mmol) at RT under inert atmosphere. The reaction mixture was stirred at 70° C. for 12 h. The mixture was quenched with water and extracted with EtOAc (2×50 mL). The combined organic phases were washed with brine, dried over anhydrous Na$_2$SO$_4$, and concentrated under reduced pressure to give crude material. The crude material was purified by column chromatography (SiO$_2$, 100-200 mesh) eluting with 15% EtOAc/hexane to afford 5 (50 mg, 0.14 mmol, 38%) as a solid. $^1$H NMR (500 MHz, CDCl$_3$): δ 8.23 (s, 1H), 8.07 (d, J=8.5 Hz, 1H), 7.93-7.91 (m, 2H), 7.82 (s, 1H), 6.28 (s, 1H), 2.83 (m, 1H), 0.97 (d, J=7.0 Hz, 3H), 0.63 (d, J=7.0 Hz, 3H). HPLC: 95.8%. MS (ESI): m/z 337 [M+H]$^+$.

Scheme 6

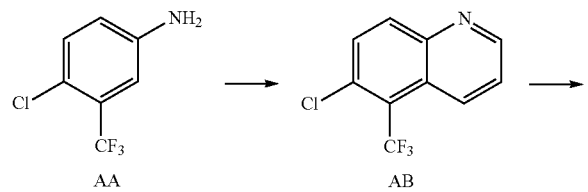

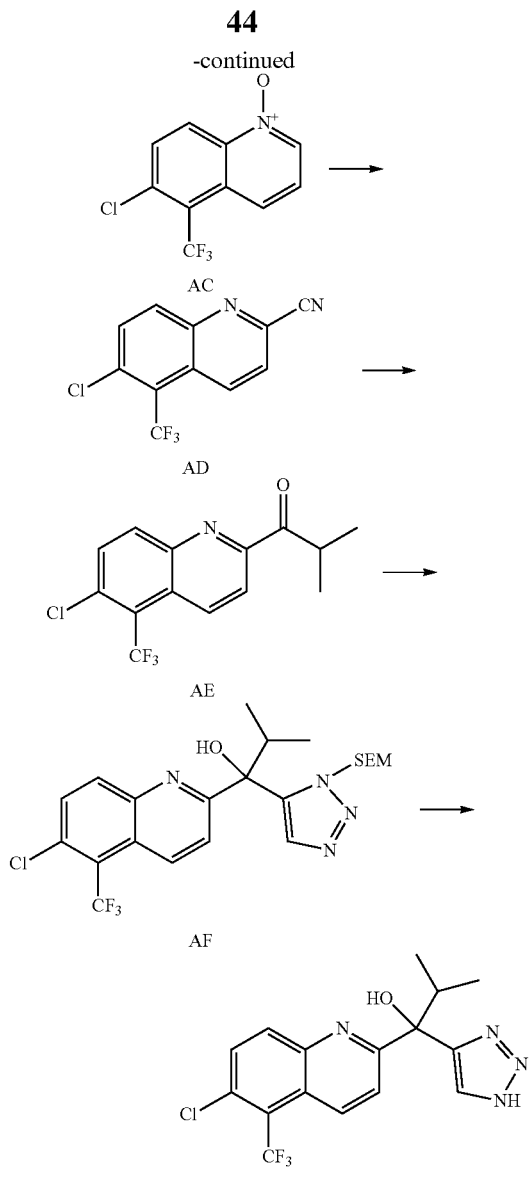

Example 6

1-(6-Chloro-5-(trifluoromethyl) quinolin-2-yl)-2-methyl-1-(1H-1,2,3-triazol-4-yl) propan-1-ol (6)

To a stirred solution of 4-chloro-3-(trifluoromethyl)aniline (AA) (10.0 g, 51.28 mmol) in glycerol (120 mL) were added sulfamix (173 g, 768 mmol), FeSO$_4$.7H$_2$O (2.9 g, 10.43 mmol) and boric acid (5 g, 80.9 mmol) at RT. The reaction mixture was then cooled to 0° C. and added Con.H$_2$SO$_4$ (35 mL) slowly portion wise under inert atmosphere. The resulting reaction mixture was heated up to 140-145° C. and stirred for 3 h. After the consumption of starting material (by TLC), the reaction mixture was cooled to RT, quenched with aq.NaHCO$_3$ and extracted with CH$_2$Cl$_2$ (3×300 mL). The combined organic extracts were washed with water (300 mL), brine (200 mL), dried over anhydrous Na$_2$SO$_4$ and concentrated under reduced pressure. The obtained crude was purified by silica gel column chromatography using 30% EtOAc/Hexane as eluent to afford quinoline AB (mixture of 5,6 & 6,7 regiomers) (65 g, 280.6 mmol, 55%) as amber colored liquid. The product formation was confirmed by crude ¹H-NMR and taken further for next reaction.

To a stirred solution of quinoline AB (13 g, 56.27 mmol) in EtOAc (100 mL) at 0° C. was added mCPBA (24.2 g, 140.28 mmol) (60% dispersion in water) and stirred at RT for 12 h. After consumption of the starting material (by TLC), the precipitated solid was filtered, washed with EtOAc and dried under reduced pressure to afford N-oxide AC (10 g) as crude yellowish solid. This material was directly taken up for next reaction without further characterization.

To a stirred solution of N-oxide AC (10 g, 40.48 mmol) in ACN (100 mL) was added Et₃N (19 mL, 141.7 mmol) followed by TMSCN (19.4 mL, 141.7 mmol) at 0° C. under an inert atmosphere. The resulting reaction mixture was stirred at RT for 16 h. After the consumption of starting material (by TLC), the volatiles were removed under reduced pressure and the crude was purified by silica gel column chromatography using 5% EtOAc/hexane to afford desired AD (5,6-isomer) (1.8 g, 7.01 mmol, 17.3%) as yellowish solid. ¹H NMR (500 MHz, CDCl3): δ 8.75 (d, J=8.5 Hz, 1H), 8.25 (d, J=9.5 Hz, 1H), 7.87 (d, J=9.0 Hz, 1H), 7.83 (d, J=9.0 Hz, 1H).

To a stirred solution of AD (1.0 g, 3.9 mmol) in toluene (15 mL) was added catalytic amount of CuBr at RT under N₂ atmosphere. The reaction mixture was cooled to −78° C.; isopropyl magnesium bromide (9.5 mL, 9.7 mmol) was then added to the reaction mixture drop wise and the stirring was continued for another 30 min at −78° C. After the consumption of starting material (by TLC), the reaction mixture was quenched with saturated NH₄Cl solution and extracted with EtOAc (2×100 mL). The combined organic extracts were dried over anhydrous Na₂SO₄ and concentrated under reduced pressure. The crude material was purified by silica gel column chromatography using 10% EtOAc/Hexane as eluent to afford ketone AE (0.6 g, 1.98 mmol, 54.5%) as yellowish solid. This material was directly taken up for next reaction without further characterization.

To a stirred solution of SEM triazole (0.79 g, 3.96 mmol) in dry ether (10 mL) was added tert-BuLi (1.9 mL, 37.48 mmol) drop wise at −78° C. and stirred for 1 h. A solution of ketone AE (0.3 g, 9.96 mmol) in ether (10 mL) was added to the reaction mixture at 0° C. and stirring was continued for another 20 min. After consumption of the starting material (by TLC), the reaction mixture was quenched with saturated NH₄Cl solution and extracted with EtOAc (2×50 mL). The combined organic extracts were washed with water (30 mL), dried over anhydrous Na₂SO₄ and concentrated under reduced pressure to afford AF (0.5 g) as crude yellowish syrupy mass. This material was directly taken up for next reaction without further purification and characterization.

To a stirred solution of AF (0.5 g, 1.0 mmol) in THF (10 mL) was added CsF (0.462 g, 3.0 mmol) followed by 1M solution of TBAF (0.26 g, 1.00 mmol) in THF at RT. The reaction mixture was heated to reflux and stirred for 18 h. After consumption of the starting material (by TLC), the reaction mixture was quenched with water (50 mL) and extracted with EtOAc (2×50 mL). The combined organic extracts were washed with water (2×50 mL), brine solution (50 mL), dried over anhydrous Na₂SO₄ and concentrated under reduced pressure. The crude material was purified by silica gel column chromatography using 30% EtOAc/hexane as eluent to afford 6 (52 mg, 0.14 mmol, 14%) as off-white solid. ¹H NMR (500 MHz, CDCl₃): δ 11.60-11.58 (br s, 1H), 8.61 (d, J=9.0 Hz, 1H), 8.17 (d, J=9.5 Hz, 1H), 8.05-8.03 (m, 1H), 7.82 (s, 1H), 7.76 (d, J=9.0 Hz, 1H), 6.17 (s, 1H), 2.83-2.82 (m, 1H), 0.97 (d, J=6.5 Hz, 3H), 0.65 (d, J=7.0 Hz, 3H). HPLC: 96.22%. MS (ESI): m/z 370 [M⁺].

Scheme 7

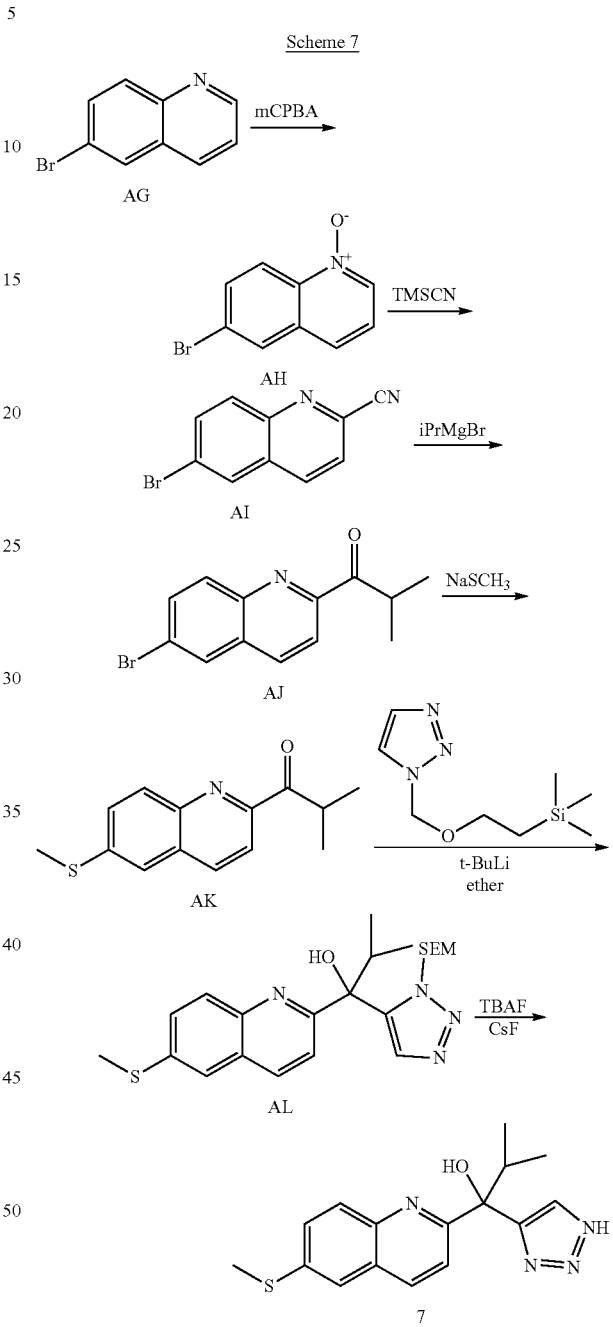

Example 7

2-Methyl-1-(6-(methylthio) quinolin-2-yl)-1-(1H-1,2,3-triazol-4-yl) propan-1-ol (7)

To a stirred solution of 6-bromoquinoline (AG) (15 g, 72.11 mmol) in EtOAc (200 mL) at 0° C. was added mCPBA (24.8 g, 143.7 mmol) (60% dispersion in water) and stirred at RT for 8 h. After consumption of the starting material (by TLC), the precipitated solid was filtered, washed with EtOAc and dried under reduced pressure to afford N-oxide AH (14 g) as crude material. This material was directly taken up for next reaction without further characterization. MS (ESI): m/z 226 [M$^+$+2].

To a stirred solution of N-oxide AH (14 g, crude) in ACN (100 mL) was added Et$_3$N (30.9 mL, 218.7 mmol) followed TMSCN (27 mL, 218.7 mmol) at 0° C. under an inert atmosphere. The reaction mixture was stirred at RT for 16 h. After the consumption of starting material (by TLC), the volatiles were removed under reduced pressure and purified by column chromatography using 20% EtOAc/hexane to afford AI (8 g, 34.3 mmol, 54.7%) as brownish solid. $^1$H NMR (500 MHz, CDCl$_3$): δ 8.23 (d, J=8.5 Hz, 1H), 8.07 (d, J=2 Hz, 1H), 8.04 (d, J=9.5 Hz, 1H), 7.91 (dd, J=2.0, 9.0 Hz, 1H), 7.72 (d, J=8.5 Hz, 1H).

To a stirred solution of AI (6 g, 25.64 mmol) in toluene (100 mL) was added catalytic amount of CuBr at RT under N$_2$ atmosphere. The reaction mixture was cooled to 0° C.; isopropyl magnesium bromide (64 mL, 64.10 mmol) was then added to the reaction mixture drop wise and the stirring was continued for another 1 h. After the consumption of starting material (by TLC), the reaction mixture was quenched with saturated NH$_4$Cl solution and extracted with EtOAc (2×100 mL). The combined organic extracts were dried over anhydrous Na$_2$SO$_4$ and concentrated under reduced pressure. The crude was purified by column chromatography using 10% EtOAc/hexane as eluent to afford ketone AJ (3 g, 10.78 mmol, 41.89%) as off-white solid. $^1$H NMR (500 MHz, CDCl$_3$): δ 8.18-8.12 (m, 2H), 8.06-8.03 (m, 2H), 7.84 (dd, J=2.0, 9.0 Hz, 1H), 4.36-4.31 (m, 1H), 1.26 (d, J=7 Hz, 6H). LCMS: m/z 280.0 [M$^+$+2] at 13.44 RT (83.06% purity).

To a stirred solution of 1-(6-Bromoquinolin-2-yl)-2-methylpropan-1-one (AJ) (2 g, 7.19 mmol) in DMF (20 mL) was added NaSCH$_3$ (0.75 mg, 10.79 mmol) at RT under an inert atmosphere. The resultant reaction mixture was stirred for 16 h at 80° C. After consumption of the starting material (by TLC), the reaction was diluted with water and extracted with EtOAc (2×30 mL). The combined organic phases were dried over anhydrous Na$_2$SO$_4$, filtered and concentrated in vacuo. The obtained crude material was purified by silica gel column chromatography eluting with 5% EtOAc/hexane to afford AK (0.7 g, 2.85 mmol, 39.77%) as a solid. $^1$H NMR (500 MHz, CDCl$_3$): δ 8.13-8.08 (m, 2H), 8.05 (d, J=9.0 Hz, 1H), 7.63 (dd, J=2.5, 9.0 Hz, 1H), 7.52 (d, J=2.0 Hz, 1H), 4.38-4.33 (m, 1H), 2.61 (s, 3H), 1.26 (d, J=7.5 Hz, 6H).

To a stirred solution of SEM triazole (1.5 g, 7.34 mmol) in dry ether (20 mL) was added n-BuLi (4.3 mL, 7.34 mmol) (1.6 M solution in hexane) drop wise and allowed to stir at −78° C. for 1 h under inert atmosphere. A solution of 2-methyl-1-(6-(methylthio) quinolin-2-yl) propan-1-one (AK) (0.3 g, 1.22 mmol) in ether (10 mL) was added to the reaction mixture at −78° C. and the stirring was continued for another 2 h at 0° C. After consumption of the starting material (by TLC), the reaction mixture was quenched with saturated NH$_4$Cl solution and extracted with EtOAc (2×50 mL). The combined organic extracts were washed with water, dried over anhydrous Na$_2$SO$_4$ and concentrated under reduced pressure to afford AL (1 g) as crude amber colored syrupy mass. This material was directly taken up for next reaction without further characterization.

To a stirred solution of 2-methyl-1-(6-(methylthio) quinolin-2-yl)-1-(1-((2-(trimethylsilyl) ethoxy) methyl)-1H-1, 2,3-triazol-5-yl) propan-1-ol (AL) (1 g, 2.25 mmol) in THF (20 mL) was added CsF (1.02 g, 6.75 mmol) followed by TBAF (2.24 mL, 2.25 mmol) (1M solution in THF) at RT under inert atmosphere. The reaction mixture was heated to 80° C. and stirred for 16 h. After consumption of the starting material (by TLC), the reaction mixture was diluted with water (30 mL) and extracted with EtOAc (3×30 mL). The combined organic layer was washed with water, dried over anhydrous Na$_2$SO$_4$ and concentrated under reduced pressure. The obtained crude product was purified by silica gel column chromatography using 30% EtOAc/Hexane as eluent to afford 7 (70 mg, 0.22 mmol, 9.9%). $^1$H NMR (500 MHz, CDCl$_3$): δ 11.65-11.63 (br s, 1H), 8.04 (d, J=8.5 Hz, 1H), 7.95 (d, J=9.0 Hz, 1H), 7.80 (br s, 2H), 7.59 (dd, J=2.0, 9.0 Hz, 1H), 7.52-7.51 (m, 1H), 6.54 (s, 1H), 2.82-2.80 (m, 1H), 2.58 (s, 3H), 0.97 (d, J=6.5 Hz, 3H), 0.63 (d, J=6.5 Hz, 3H). HPLC: 95.12%. MS (ESI): m/z 315 [M$^+$+1].

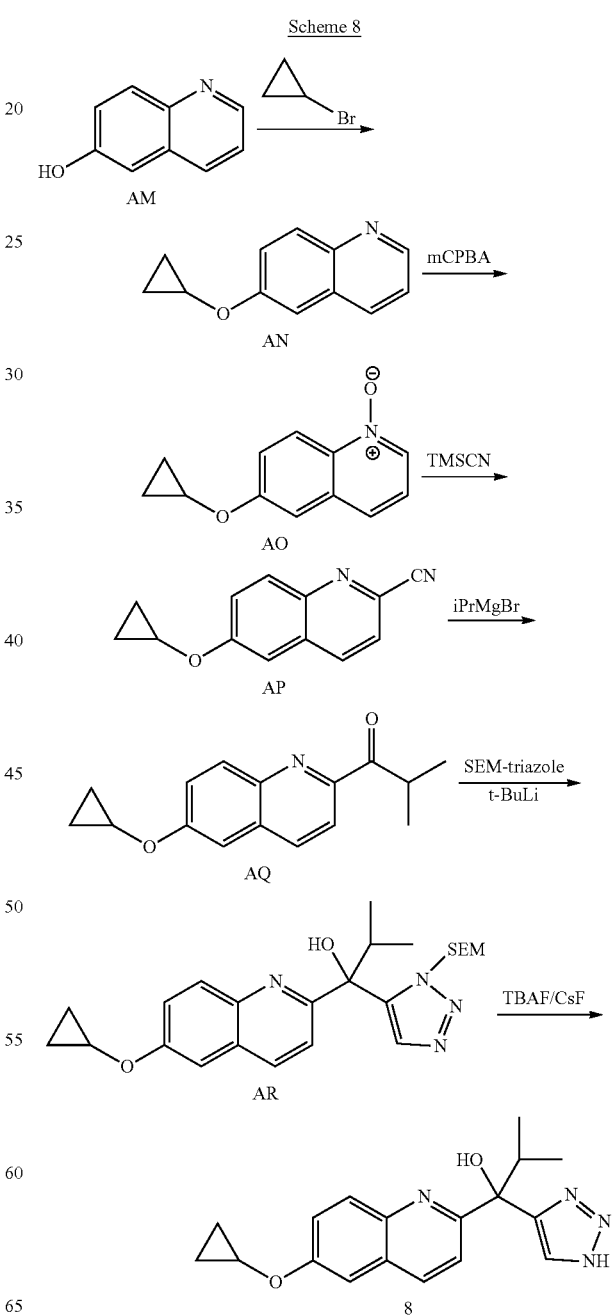

Scheme 8

Example 8

1-(6-Cyclopropoxyquinolin-2-yl)-2-methyl-1-(1H-1,2,3-triazol-4-yl)propan-1-ol (8)

To a stirred solution of 6-hydroxyquinoline (AM) (0.5 g, 3.44 mmol) in DMF (10 mL) was added KO$^t$Bu (1.15 g, 10.32 mmol) at RT. After being stirred for 4 h at RT, cyclo propyl bromide (1.24 g, 10.32 mmol) was added to the reaction mixture and heated at 80° C. for 24 h. After consumption of the starting material by TLC, the reaction mixture was diluted with water (100 mL) and extracted with EtOAc (3×50 mL). The combined organic extracts were washed with brine, dried over anhydrous $Na_2SO_4$ and concentrated under reduced pressure. The crude material was purified by silica gel column chromatography to afford AN (0.1 g, 0.54 mmol, 15.7%) as light yellow solid. $^1$H NMR (200 MHz, $CDCl_3$): δ 8.78-8.76 (m, 1H), 8.10-7.98 (m, 2H), 7.43-7.33 (m, 3H), 3.91-3.82 (m, 1H), 0.94-0.85 (m, 4H).

To a stirred solution of AN (0.1 g, 0.54 mmol) in EtOAc (5 mL) was added m-CPBA (0.18 g, 1.08 mmol) at 0° C. and stirred at RT for 14 h. After consumption of the starting material (by TLC), the reaction mixture was concentrated under reduced pressure. The crude material was purified by silica gel column chromatography to afford N-oxide AO (0.1 g, 0.49 mmol, 92.1%) as a light reddish solid. This compound was directly used for next reaction.

To a stirred solution of N-oxide AO (0.1 g, 0.49 mmol) in ACN (5 mL) was added $Et_3N$ (2.6 mL, 1.71 mmol) followed by TMSCN (0.25 mL, 1.71 mmol) at 0° C. under an inert atmosphere. The reaction mixture was stirred at RT for 16 h. The volatiles were evaporated under reduced pressure and the crude material was purified by silica gel column chromatography to afford AP (80 mg, 0.36 mmol, 73%) as off-white solid. $^1$H NMR (500 MHz, $CDCl_3$): δ 8.18 (d, J=8.5 Hz, 1H), 8.05 (d, J=9.0 Hz, 1H), 7.65 (d, J=8.0 Hz, 1H), 7.47 (dd, J=8.5, 2.5 Hz 1H), 7.42 (s, 1H), 3.91-3.88 (m, 1H), 0.93-0.85 (m, 4H).

To a stirred solution of AP (0.2 g, 0.95 mmol) in toluene (5 mL) was added catalytic amount of CuBr at RT under $N_2$ atmosphere. The reaction mixture was cooled to −78° C.; isopropyl magnesium bromide (2.4 mL, 2.37 mmol) was then added to the reaction mixture drop wise and the stirring was continued for another 1 h at 0° C. After the consumption of starting material (by TLC), the reaction mixture was quenched with saturated $NH_4Cl$ solution and extracted with EtOAc (2×100 mL). The combined organic extracts were washed with water, brine, dried over anhydrous $Na_2SO_4$ and concentrated under reduced pressure. The obtained crude material was purified by silica gel column chromatography eluting with 20% EtOAc/hexane to afford ketone AQ (0.1 g, 0.39 mmol, 41.66%) as low melting yellow solid.

$^1$H NMR (500 MHz, $CDCl_3$): δ 8.15 (d, J=8.5 Hz, 1H), 8.10-8.06 (m, 2H), 7.42-7.40 (m, 2H), 4.38-4.34 (m, 1H), 3.90-3.88 (m, 1H), 1.26 (d, J=7.0 Hz, 6H), 0.90-0.85 (m, 4H).

To a stirred solution of SEM triazole (0.62 g, 3.13 mmol) in dry ether (6 mL) was added tert-BuLi (2.9 mL, 11.89 mmol, 1.6 M solution in hexane) drop wise and allowed to stir at −78° C. for 1 h under inert atmosphere. A solution of 1-(6-cyclopropoxyquinolin-2-yl)-2-methylpropan-1-one (AQ) (0.2 g, 0.78 mmol) in ether (6 mL) was added to the reaction mixture at −78° C. and the stirring was continued for another 30 min. After consumption of the starting material (by TLC), the reaction mixture was quenched with saturated $NH_4Cl$ solution and extracted with EtOAc (3×15 mL). The combined organic extracts were washed with brine, dried over anhydrous $Na_2SO_4$ and concentrated under reduced pressure. The obtained crude material was purified by silica gel column chromatography eluting with 30% EtOAc/hexane to afford AR (0.35 g) as crude yellowish thick syrupy mass. This material was used in the deprotection step without further characterization.

To a stirred solution of 1-(6-cyclopropoxyquinolin-2-yl)-2-methyl-1-(1-((2-(trimethylsilyl) ethoxy) methyl)-1H-1,2,3-triazol-5-yl)propan-1-ol (AR) (0.35 g, 0.77 mmol) in THF (5 mL) was added CsF (0.42 g, 3.08 mmol) followed by TBAF (1 mL, 0.77 mmol, 1M solution in THF) at RT and stirred under reflux for 12 h under inert atmosphere. After consumption of the starting material (by TLC), the reaction mixture was quenched with water (20 mL) and extracted with EtOAc (3×30 mL). The combined organic layer was washed with water, brine and dried over anhydrous $Na_2SO_4$ and concentrated under reduced pressure. The obtained crude product was purified by silica gel column chromatography using 30% EtOAc/hexane as eluent to afford 8 (85 mg, 0.26 mmol, 33%) as off-white solid. $^1$H NMR (500 MHz, $CDCl_3$): δ 11.82-11.60 (br s, 1H), 8.08 (d, J=9.0 Hz, 1H), 7.97 (d, J=10.0 Hz, 1H), 7.81 (br s, 2H), 7.38-7.36 (m, 2H), 6.62 (s, 1H), 3.85-3.84 (m, 1H), 2.82-2.80 (m, 1H), 0.98 (d, J=7.0 Hz, 3H), 0.87-0.83 (m, 4H), 0.64 (d, J=7.0 Hz, 3H). HPLC: 98.3%. MS (ESI): m/z 325.9 [M$^+$+1].

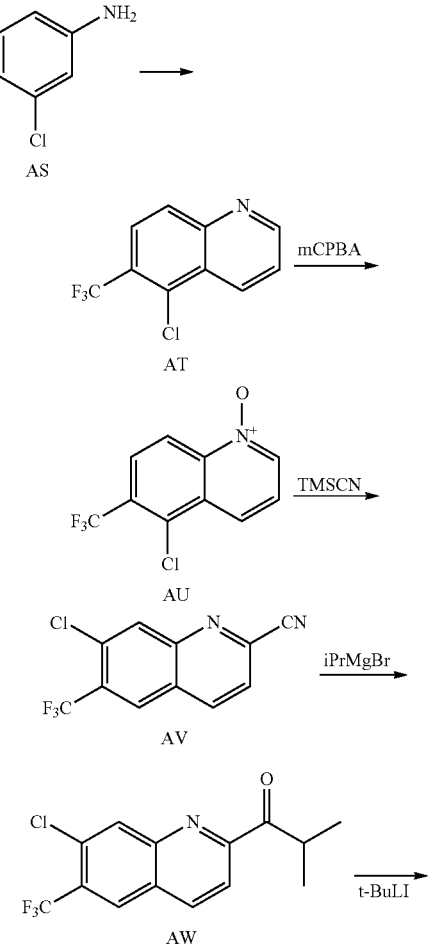

Scheme 9

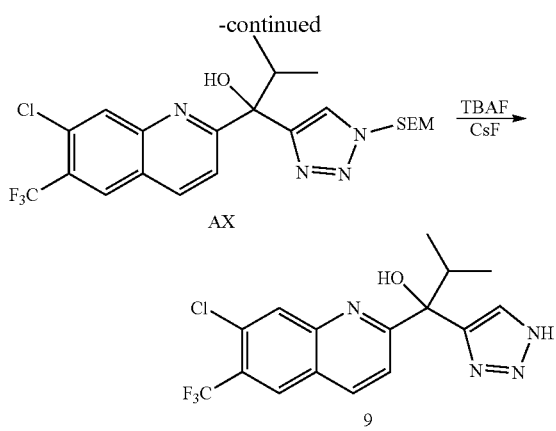

Example 9

1-(7-Chloro-6-(trifluoromethyl) quinolin-2-yl)-2-methyl-1-(1H-1,2,3-triazol-4-yl) propan-1-ol (9)

To a stirred solution of 3-chloro-4-(trifluoromethyl)aniline (AS) (10 g, 51.2 mmol) in glycerol (120 mL) were added sulfamix (17.3 g, 76.8 mmol), FeSO$_4$.7H$_2$O (2.9 g, 10.7 mmol) followed by boric acid (5.06 g, 81.9 mmol) at RT. The reaction mixture was cooled to 0° C.; Conc.H$_2$SO$_4$ (35 mL) was added to the reaction mixture and heated at 145° C. for 3 h. After consumption of the starting material (by TLC), the reaction was quenched with cold water and neutralized with NaHCO$_3$. The aqueous layer was extracted with CH$_2$Cl$_2$ (3×500 mL). The combined organic phases were washed with water (100 mL), brine (100 mL), dried over anhydrous Na$_2$SO$_4$, filtered and concentrated in vacuo. The obtained crude material was purified by silica gel column chromatography eluting with 30% EtOAc/hexane to afford AT (mixture of 5,6- and 6,7-regio isomers) (4 g, 17.2 mmol, 34%) as syrup.

To a stirred solution of AT (mixture of 5,6- and 6,7-regio isomers) (4 g, 17.2 mmol) in EtOAc (20 mL) was added m-CPBA (7.4 g, 43 mmol) at 0° C. and the reaction mixture was stirred at RT for 12 h. After consumption of the starting material (by TLC), the reaction mixture was concentrated under reduced pressure. The crude material was purified by silica gel column chromatography eluting with 10% MeOH/CH$_2$Cl$_2$ to afford AU (mixture of 5,6- and 6,7-regio isomers) (2 g, 8.06 mmol, 47.6%) as yellow solid.

To a stirred solution of AU (mixture of 5,6- and 6,7-regio isomers) (5.0 g, 20.1 mmol) in ACN (50 mL) was added Et$_3$N (7.1 g, 70.3 mmol) followed by TMSCN (6.9 g, 70.3 mmol) at 0° C. under an inert atmosphere. The reaction mixture was stirred at RT for 14 h. The volatiles were evaporated under reduced pressure and the crude material was purified by silica gel column chromatography eluting with 8% EtOAc/Hexane to afford AV (6,7-isomer) (2.0 g, 7.75 mmol, 38.4%) as a brown solid.

To a stirred solution of AV (0.3 g, 1.16 mmol) in toluene (10 mL) was added catalytic amount of CuBr (30 mg) at RT under N$_2$ atmosphere. The reaction mixture was cooled to −40° C.; isopropyl magnesium bromide (0.5 g, 3.48 mmol) was then added to the reaction mixture drop wise and the stirring was continued for another 1 h. The reaction mixture was quenched with saturated NH$_4$Cl solution and filtered through celite bed. The filtrate was extracted with ethyl acetate (2×25 mL); combined organic extracts were washed with brine, dried over anhydrous Na$_2$SO$_4$ and concentrated under reduced pressure. The crude material was purified by silica gel column chromatography eluting with 3% EtOAc/Hexane to afford ketone AW (0.11 g, 0.36 mmol, 31%) as yellow solid. $^1$H NMR (500 MHz, CDCl$_3$): δ 8.36 (s, 1H), 8.35 (d, J=9 Hz, 1H), 8.26 (s, 1H), 8.20 (d, J=8.5 Hz, 1H), 4.31-4.28 (m, 1H), 1.29-1.26 (m, 6H).

To a stirred solution of SEM triazole (1.0 g, 5.32 mmol) in dry ether (20 mL) was added tert-BuLi (3.12 mL, 5.32 mmol) drop wise at −78° C. and stirred for 4 h. A solution of 1-(7-chloro-6-(trifluoromethyl)quinolin-2-yl)-2-methyl-propan-1-one (AW) (0.4 g, 1.32 mmol) in ether (10 mL) was added to the reaction mixture at −78° C. and stirring was continued for another 30 min. After consumption of the starting material (by TLC), the reaction mixture was quenched with saturated NH$_4$Cl solution and the aqueous layer was extracted with CH$_2$Cl$_2$ (2×50 mL). The combined organic extracts were dried over anhydrous Na$_2$SO$_4$ and concentrated under reduced pressure to afford AX (1.3 g) as crude pale yellow liquid. This material was used in the next step without further characterization.

To a stirred solution of AX (1.3 g, 2.6 mmol) in THF (26 mL) at RT was added CsF (1.1 g, 7.8 mmol) followed by TBAF (2.5 mL, 2.6 mmol, 1M in THF) and stirred under reflux for 16 h. After consumption of the starting material (by TLC), the reaction mixture was quenched with water (100 mL) and extracted with EtOAc (2×30 mL). The combined organic extracts were dried over anhydrous Na$_2$SO$_4$ and concentrated under reduced pressure. The crude material was purified by silica gel column chromatography eluting with 10% EtOAc/hexane and purified by Prep.TLC to afford 9 (65 mg, 0.17 mmol, 6.7%) as yellowish thick syrupy mass.

$^1$H NMR (500 MHz, CDCl$_3$): δ 8.26-8.20 (m, 3H), 8.03 (d, J=8.5 Hz, 1H), 7.83 (s, 1H), 6.20 (s, 1H), 2.86-2.84 (m, 1H), 0.97 (d, J=6.5 Hz, 3H), 0.63 (d, J=6.5 Hz, 3H). HPLC: 93.67%. MS (ESI): m/z 369 [M$^+$−1].

Scheme 10

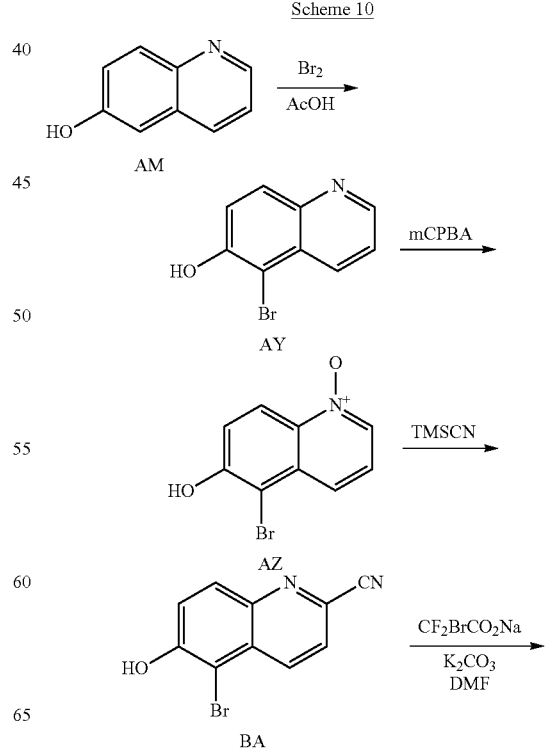

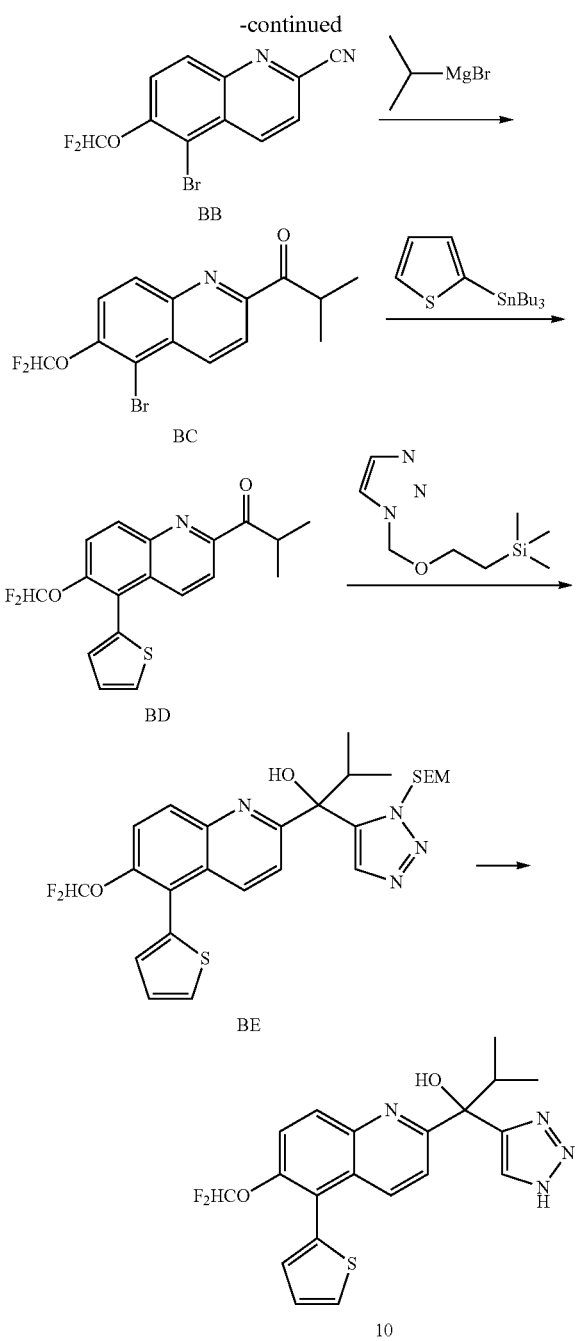

reduced pressure. The crude was purified by silica gel column chromatography using 30% EtOAc/hexane as eluent to afford AY (1.3 g, 5.80 mmol, 43%) as off-white solid. $^1$H NMR (500 MHz, CDCl$_3$): δ 8.80 (d, J=4.0 Hz, 1H), 8.37 (d, J=8.0 Hz 1H), 8.03 (d, J=9.0 Hz, 1H), 7.52-7.47 (m, 2H), 6.19-6.17 (br s, 1H). LCMS: m/z 225.9 [M$^+$+1] at 5.12 RT (92.56% purity).

To a stirred solution of AY (1.1 g, 4.91 mmol) in EtOAc (30 mL) at 0° C. was added mCPBA (2.1 g, 12.27 mmol) (60% dispersion in water) and stirred at RT for 16 h. After consumption of the starting material (by TLC), the precipitated solid was filtered, washed with EtOAc and dried under reduced pressure to afford N-oxide AZ (1 g, 4.16 mmol, 84%) as pure off-white solid. $^1$H NMR (500 MHz, DMSO-d6): δ 11.24 (s, 1H), 8.46-8.44 (m, 2H), 7.90 (d, J=8.5 Hz, 1H), 7.52-7.49 (m, 2H). MS (ESI): m/z 240 [M$^+$], 242 [M$^+$+2].

To a stirred solution of N-oxide AZ (0.9 g, 3.72 mmol) in ACN (30 mL) was added Et$_3$N (1.87 mL, 12.98 mmol) followed by TMSCN (1.87 mL, 12.98 mmol) at 0° C. under an inert atmosphere. The resulting reaction mixture was stirred at RT for 16 h. After the consumption of starting material (by TLC), the volatiles were removed under reduced pressure and purified by column chromatography using 30% EtOAc/Hexane as eluent to afford BA (0.9 g, 3.61 mmol, 97%) as off-white solid. $^1$H NMR (500 MHz, CDCl$_3$): δ 8.47 (d, J=8.5 Hz, 1H), 8.09 (d, J=9.5 Hz, 1H), 7.77 (d, J=9.0 Hz, 1H), 7.62 (d, J=9.5 Hz, 1H), 6.21-6.20 (br s, 1H).

To a stirred solution of BA (9 g, 36 mmol) in DMF (90 mL) were added BrCF$_2$CO$_2$Na (28.3 g, 144 mmol) and K$_2$CO$_3$ (29.8 g, 216 mmol) at RT and stirred at 80° C. for 4 h. After the consumption of starting material (by TLC), the reaction mixture was poured into ice cold water and extracted EtOAc (3×300 mL). The combined organic extracts were dried over anhydrous Na$_2$SO$_4$ and concentrated under reduced pressure to afford the crude product. The crude was purified by silica gel column chromatography using 8% EtOAc/hexane as eluent to afford BB (7 g, 23.41 mmol, 65.4%) as pale yellow solid. $^1$H NMR (500 MHz, CDCl$_3$): δ 8.76 (d, J=8.0 Hz, 1H), 8.20 (d, J=9.0 Hz, 1H), 7.83 (d, J=9.0 Hz, 1H), 7.78 (d, J=9.0 Hz, 1H), 6.72 (t, J=72.5 Hz, 1H).

To a stirred solution of BB (4.8 g, 16.05 mmol) in toluene (50 mL) was added catalytic amount of CuBr at RT under N$_2$ atmosphere. The reaction mixture was cooled to −78° C.; isopropyl magnesium bromide (40.1 mL, 40.13 mmol) was then added to the reaction mixture drop wise and the stirring was continued for another 30 min at −78° C. After the consumption of starting material (by TLC), the reaction mixture was quenched with saturated NH$_4$Cl solution and extracted with EtOAc (2×100 mL). The combined organic extracts were dried over anhydrous Na$_2$SO$_4$ and concentrated under reduced pressure to afford the crude product. The crude was purified by silica gel column chromatography using 2% EtOAc/hexane as eluent to afford ketone BC (2 g, 5.81 mmol, 36%) as pale yellow solid. $^1$H NMR (500 MHz, CDCl$_3$): δ 8.69 (d, J=9.0 Hz, 1H), 8.23 (d, J=9.0 Hz, 1H), 8.20 (d, J=9.0 Hz, 1H), 7.70 (d, J=9.5 Hz, 1H), 6.69 (t, J=73.0 Hz, 1H), 4.35-4.30 (m, 1H), 1.27 (d, J=7 Hz, 6H). LCMS: m/z 344.1 [M$^+$+1] at 5.18 RT (88.39% purity).

A solution of BC (1.0 g, 2.90 mmol) in 1,4-dioxane (20 mL) was purged with argon for 30 min. Then Pd(PPh$_3$)$_4$ (0.335 g, 0.29 mmol) and tributyl(thiophen-2-yl)stannane (1.38 mL, 4.06 mmol) was added to the reaction mixture and purged with argon for another 10 min. The resultant reaction mixture was stirred at 90° C. for 24 h. After consumption of

Example 10

1-(6-(Difluoromethoxy)-5-(thiophen-2-yl)quinolin-2-yl)-2-methyl-1-(1H-1,2,3-triazol-4-yl)propan-1-ol (10)

To a stirred solution of quinolin-6-ol (AM) (2.0 g, 13.77 mmol) in AcOH (20 mL) was added Br$_2$ (0.194 mL, 13.77 mmol) drop wise at RT and stirring was continued for another 1 h. The progress of the reaction was monitored by TLC. The reaction mixture was poured into ice-cold water, quenched with saturated NaHSO$_3$ solution and extracted with EtOAc (2×50 mL). The combined organic layer was dried over anhydrous Na$_2$SO$_4$ and concentrated under the starting material (by TLC), the volatiles were evaporated under reduced pressure. The crude was purified by silica gel column chromatography and then by Prep HPLC to afford BD (0.9 g, 2.59 mmol, 90%) as pale yellow solid. $^1$H NMR (500 MHz, CDCl$_3$): δ 8.26 (d, J=9.0 Hz, 2H), 8.08 (d, J=8.5 Hz, 1H), 7.73 (d, J=9.5 Hz, 1H), 7.57 (d, J=5.5 Hz, 1H), 7.26-7.23 (m, 1H), 7.13 (d, J=2.5 Hz, 1H), 6.47 (t, J=73.5 Hz, 1H), 4.39-4.33 (m, 1H), 1.27 (d, J=7.5 Hz, 6H). MS (ESI): m/z 348.3 [M$^+$+1].

To a stirred solution of SEM triazole (0.68 mL, 3.45 mmol) in dry ether (10 mL) was added t-BuLi (2 mL, 3.45 mmol) drop wise at −78° C. and stirred for 1 h. A solution of 1-(6-(difluoromethoxy)-5-(thiophen-2-yl)quinolin-2-yl)-2-methylpropan-1-one (BD) (0.3 g, 0.86 mmol) in ether (10 mL) was added the above reaction mixture and stirring was continued for another 30 min at −78° C. The reaction mixture was then quenched with saturated NH$_4$Cl solution and extracted with EtOAc (2×50 mL). The combined organic extracts were washed with water, dried over anhydrous Na$_2$SO$_4$ and concentrated under reduced pressure. The crude material was purified by silica gel column chromatography using 5% EtOAc/hexane as eluent to afford BE (0.4 g, 0.73 mmol, 84%) as a solid. This material was used in the next step without further characterization.

To a stirred solution of BE (0.409 g, 0.747 mmol) in dry THF (20 mL) was added CsF (0.331 g, 2.19 mmol) followed by TBAF (0.732 mL, 0.732 mmol) (1M solution of in THF) at RT. The reaction mixture was stirred for 16 h at 70° C. After consumption of the starting material (by TLC), the reaction mixture was quenched with water (40 mL) and extracted with EtOAc (2×50 mL). The combined organic extracts were dried over anhydrous Na$_2$SO$_4$ and concentrated under reduced pressure to afford the crude product. The crude was purified by silica gel column chromatography using 20% EtOAc/hexane as eluent to afford 10 (90 mg, 0.216 mmol, 30%) as white solid. $^1$H NMR (500 MHz, CDCl$_3$): δ 8.18-8.14 (m, 2H), 7.81 (s, 1H), 7.68 (d, J=9.0 Hz, 1H), 7.54 (d, J=5.5 Hz, 1H), 7.22-7.20 (m, 1H), 7.10 (d, J=3.0 Hz, 1H), 6.42 (t, J=74.0 Hz, 1H), 6.44 (s, 1H), 2.88-2.78 (m, 1H), 0.97 (d, J=6.5 Hz, 3H), 0.65 (d, J=6.0 Hz, 3H). HPLC: 99.46%. MS (ESI): m/z 417 [M$^+$+1].

Scheme 11

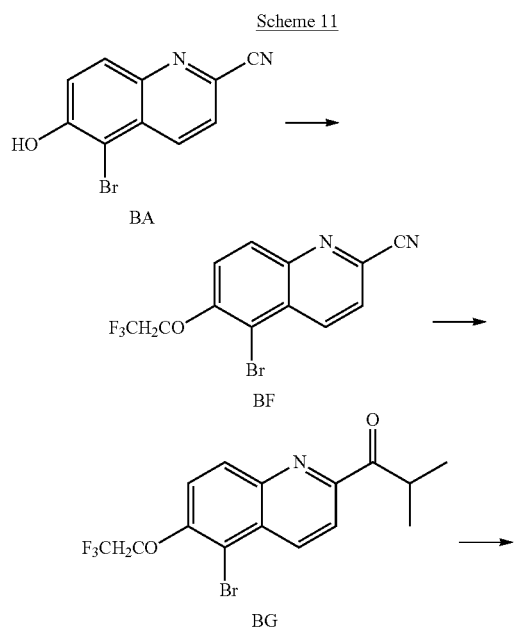

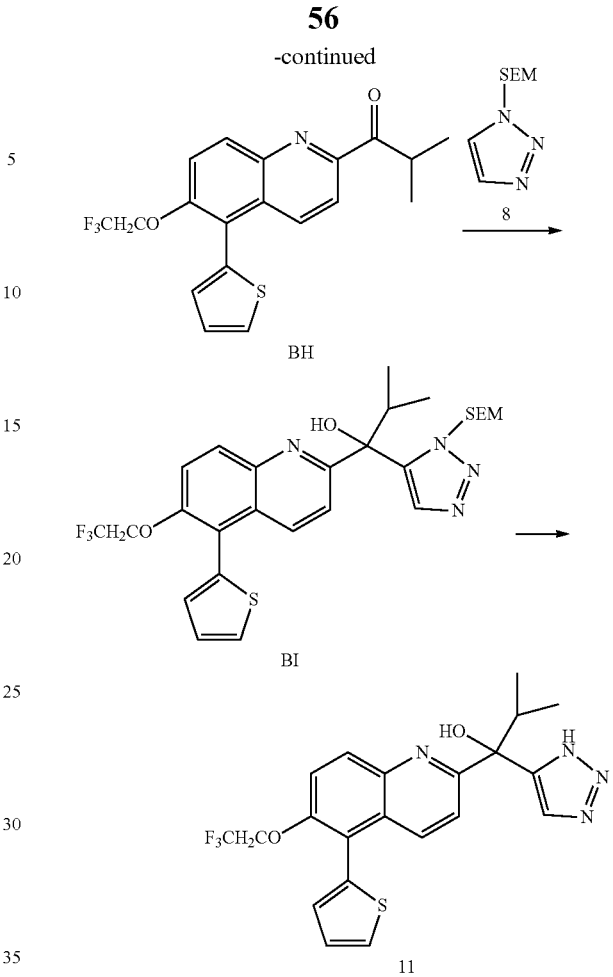

Example 11

2-Methyl-1-(5-(thiophen-2-yl)-6-(2,2,2-trifluoroethoxy)quinolin-2-yl)-1-(1H-1,2,3-triazol-5-yl)propan-1-ol (11)

To a stirred solution of BA (6 g, 24.09 mmol) in DMF (90 mL) were added 2,2,2-trifluoroethyl 4-methylbenzenesulfonate (9.1 g, 35.83 mmol) and K$_2$CO$_3$ (6.6 g, 47.82 mmol) at RT and stirred at 90° C. for 24 h. The progress of the reaction was monitored by TLC; the reaction mixture was poured into ice-cold water and extracted EtOAc (3×300 mL). The combined organic extracts were washed with water, brine, dried over anhydrous Na$_2$SO$_4$ and concentrated under reduced pressure. The crude was purified by silica gel column chromatography using 30% EtOAc/hexane as eluent to afford desired 5,6-isomer of BF (2.5 g, 7.55 mmol, 32%) as a low melting yellowish solid. $^1$H NMR (500 MHz, CDCl$_3$): δ 8.71 (d, J=8.5 Hz, 1H), 8.20 (d, J=9.5 Hz, 1H), 7.79 (d, J=9.0 Hz, 1H), 7.58 (d, J=9.5 Hz, 1H), 4.66-4.59 (m, 2H).

To a stirred solution of BF (2.5 g, 7.55 mmol) in toluene (60 mL) was added catalytic amount of CuBr at RT under N$_2$ atmosphere. The reaction mixture was cooled to −78° C.; isopropyl magnesium bromide (22 mL, 22.65 mmol) was then added to the reaction mixture drop wise and the stirring was continued for another 30 min at −5° C. After the consumption of starting material (by TLC), the reaction mixture was quenched with saturated NH$_4$Cl solution and extracted with EtOAc (2×100 mL). The combined organic extracts were washed with brine solution (100 mL), dried over anhydrous Na$_2$SO$_4$ and concentrated under reduced pressure. The crude material was purified by silica gel column chromatography using 30% EtOAc/Hexane as eluent to afford ketone BG (1.5 g, 3.98 mmol, 53%) as thick reddish syrupy mass. $^1$H NMR (500 MHz, CDCl$_3$): δ 8.65 (d, J=9.0 Hz, 1H), 8.21-8.19 (m, 2H), 7.52 (d, J=9.5 Hz, 1H), 4.62-4.57 (m, 2H), 4.35-4.29 (m, 1H), 1.27 (d, J=7.0 Hz, 6H).

A solution of BG (2 g, 5.31 mmol) in 1,4-dioxane (40 mL) was purged with argon for 10 min. Then Pd(PPh$_3$)$_4$ (0.61 g, 0.53 mmol) and Bu$_3$Sn-thiophene (2.9 mL, 7.96 mmol) were added to the reaction mixture and purged with argon for another 20 min. The resultant reaction mixture was stirred for 18 h at 80° C. After consumption of the starting material (by TLC), the volatiles were evaporated under reduced pressure. The crude material was purified by silica gel column chromatography using 15% EtOAc/Hexane as eluent to afford BH (1.0 g, 2.63 mmol, 67%) as off-white solid. $^1$H NMR (500 MHz, CDCl$_3$): δ 8.26-8.22 (m, 2H), 8.04 (d, J=9.0 Hz, 1H), 7.55 (d, J=9.0 Hz, 2H), 7.22-7.21 (m, 1H), 7.12-711 (m, 1H), 4.39-4.34 (m, 3H), 1.26 (d, J=7.0 Hz, 6H).

To a stirred solution of SEM triazole (0.55 g, 2.6 mmol) in dry ether (15 mL) was added tert-BuLi (1.5 mL, 2.5 mmol) drop wise at −78° C. and stirred for 1 h. A solution of BH (0.3 g, 0.65 mmol) in ether (10 mL) was added to the reaction mixture at −78° C. and stirring was continued for another 30 min at −78° C. The reaction mixture was quenched with saturated NH$_4$Cl solution (50 mL) and extracted with EtOAc (2×50 mL). The combined organic extracts were washed with brine (50 mL), dried over anhydrous Na$_2$SO$_4$ and concentrated under reduced pressure. The crude material was purified by silica gel column chromatography using 15% EtOAc/Hexane as eluent to afford BI (0.35 g) as crude off-white solid. This material was used in the next step without further characterization.

To a stirred solution of BI (0.35 g, 0.60 mmol) in THF (10 mL) was added CsF (0.28 g, 1.8 mmol) followed by 1M solution of TBAF (0.6 mL, 0.60 mmol) at RT. The reaction mixture was heated to reflux and stirred for 12 h. After consumption of the starting material (by TLC), the reaction mixture was quenched with water (100 mL) and extracted with EtOAc (2×50 mL). The combined organic extracts were washed with brine (100 mL), dried over anhydrous Na$_2$SO$_4$ and concentrated under reduced pressure. The crude material was purified by silica gel column chromatography using 20% EtOAc/hexane as eluent to afford 11 (85 mg, 0.18 mmol, 31%) as off-white solid. $^1$H NMR (500 MHz, CDCl$_3$): δ 12.10-11.30 (br s, 1H), 8.19 (d, J=9.5 Hz, 1H), 8.13 (d, J=9.5 Hz, 1H), 7.80 (d, J=5.0 Hz, 2H), 7.54-7.50 (m, 2H), 7.21-7.19 (m, 1H), 7.10-7.09 (m, 1H), 6.49 (s, 1H), 4.34-4.29 (m, 2H), 2.82-2.79 (m, 1H), 0.97 (d, J=6.5 Hz, 3H), 0.65 (d, J=7.0 Hz, 3H). MS (ESI): m/z 449 [M$^+$+1]. HPLC: 94.03%.

The following examples were synthesized using similar procedures as described above using appropriately modified reagents and/or starting materials.

Example 12

2-methyl-1-(1H-1,2,3-triazol-4-yl)-1-(6-(2,2,2-trifluoroethoxy)naphthalen-2-yl)propan-1-ol (12)

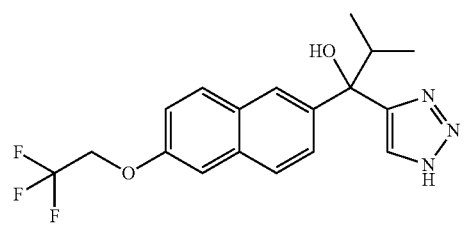

MS (ESI): m/z 366 [M$^+$+1]. HPLC Retention Time: 2.45 min.

Example 13

1-(6-(difluoromethoxy)naphthalen-2-yl)-2-methyl-1-(1H-1,2,3-triazol-4-yl)propan-1-ol (13)

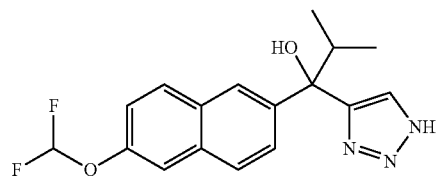

HPLC Retention Time: 4.96 min.

Example 14

1-(6-methoxyquinolin-2-yl)-2-methyl-1-(1H-1,2,3-triazol-4-yl)propan-1-ol (14)

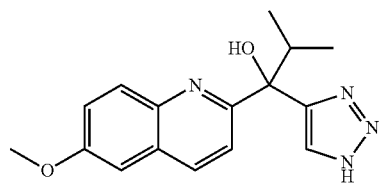

MS (ESI): m/z 299 [M$^+$+1]. HPLC Retention Time: 1.82 min.

Example 15

2-methyl-1-(1H-1,2,3-triazol-4-yl)-1-(6-(2,2,2-trifluoroethoxy)quinolin-2-yl)propan-1-ol (15)

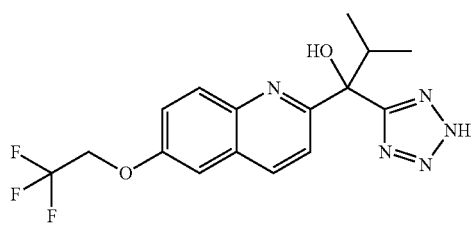

MS (ESI): m/z 367 [M$^+$+1]. HPLC Retention Time: 2.40 min.

Example 16

1-(6,7-difluoroquinolin-2-yl)-2-methyl-1-(1H-1,2,3-triazol-4-yl)propan-1-ol (16)

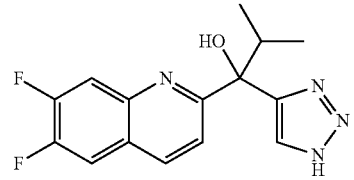

MS (ESI): m/z 305 [M$^+$+1]. HPLC Retention Time: 2.28 min.

Example 17

2-methyl-1-(1H-1,2,3-triazol-4-yl)-1-(6-(trifluoromethoxy)quinolin-2-yl)propan-1-ol (17)

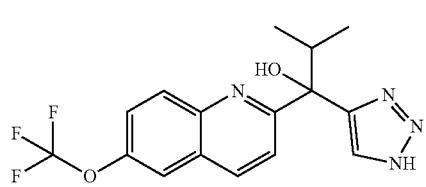

MS (ESI): m/z 353 [M$^+$+1]. HPLC Retention Time: 2.52 min.

Example 18

1-(5,6-dichloroquinolin-2-yl)-2-methyl-1-(1H-1,2,3-triazol-4-yl)propan-1-ol (18)

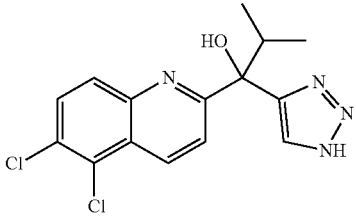

MS (ESI): m/z 337 [M$^+$+1]. HPLC Retention Time: 2.72 min.

Example 19

1-(5-chloro-6-(difluoromethoxy)quinolin-2-yl)-2-methyl-1-(1H-1,2,3-triazol-4-yl)propan-1-ol (19)

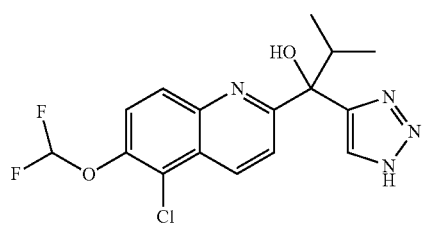

MS (ESI): m/z 369 [M$^+$+1]. HPLC Retention Time: 2.55 min.

Example 20

1-(6,7-bis(difluoromethoxy)quinolin-2-yl)-2-methyl-1-(1H-1,2,3-triazol-4-yl)propan-1-ol (20)

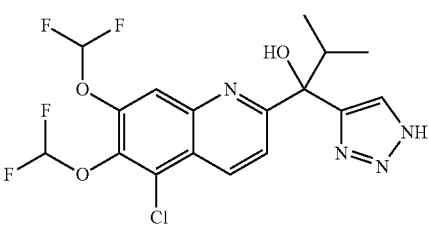

MS (ESI): m/z 401 [M$^+$+1]. HPLC Retention Time: 2.48 min.

Example 21

1-(5-chloro-6-(trifluoromethoxy)quinolin-2-yl)-2-methyl-1-(1H-1,2,3-triazol-4-yl)propan-1-ol (21)

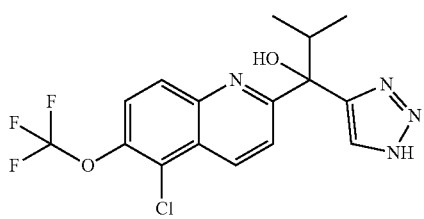

MS (ESI): m/z 387 [M$^+$+1]. HPLC Retention Time: 2.88 min.

Example 22

1-(6-(4-fluorophenyl)-5-(trifluoromethyl)quinolin-2-yl)-2-methyl-1-(1H-1,2,3-triazol-4-yl)propan-1-ol (22)

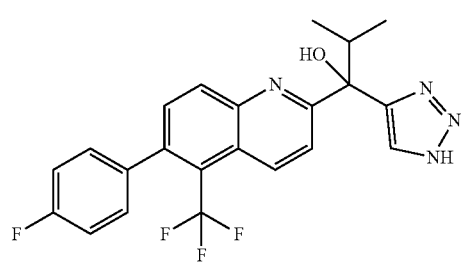

MS (ESI): m/z 431 [M$^+$+1]. HPLC Retention Time: 2.92 min.

Example 23

2-(1-hydroxy-2-methyl-1-(1H-1,2,3-triazol-4-yl)propyl)-5-(trifluoromethyl)quinoline-6-carbonitrile (23)

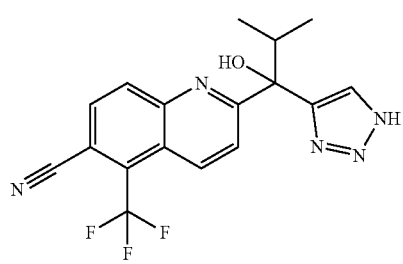

MS (ESI): m/z 360 [M$^+$-1]. HPLC Retention Time: 2.38 min.

Example 24

Whole-Cell Competition Assay

HEK293 cells were transfected with pcDNA-AR vector using FuGENE6 Reagent (Promega). Cells (100,000 cells) were then seeded in DMEM supplemented with 8% charcoal-stripped fetal calf serum (FCS) on 24-well plates coated with 0.2% gelatin (Sigma-Aldrich). Following overnight incubation, cells were treated with the appropriate competitor ligand in the presence of 0.1 nM [$^3$H]—R1881 for 2 hours. Cells were then lysed in 200 µl lysis buffer (2% SDS, 10% glycerol, and 10 mM Tris-HCl, pH 6.8) and diluted with an additional 300 µl of 10 mM Tris-HCl (pH 8.0). Each sample (300 µl) was added to 3 ml Cytoscint (MP Biomedicals) and analyzed by scintillation counting (Beckman LS 6000SC). Data were normalized to total protein for each sample and measured by the Pierce BCA Protein Assay Kit (Thermo Fisher Scientific) following the manufacturer's instructions.

Example 25

AR Reporter Gene Assay

CV1 cells were seeded in 96-well plates and transfected using Lipofectin Reagent (Invitrogen, Thermo Fisher Scientific) as described in the manufacturer's instructions. The DNA mixture for each 96-well plate consisted of 100 ng pcDNA-AR (WT, T877A, W741C, or F876L), 2,400 ng MMTV-Luc (or PSA-Luc), and 500 ng Renilla-Luc. After overnight incubation, cells were treated with hormone for 24 hours. Cells were then lysed and quantified for luciferase activity using a dual-luciferase reagent.

Example 26

AR Expression Across Tumor Types

Androgen receptor (AR) expression data obtained via RNA sequencing from The Cancer Genome Atlas (TCGA; https://cancergenome.nih.gov/) were analyzed using the visualization tool, cBioporta (http://www.cbioportal.org/) according to Cerami et al. 2012 (The cBio Cancer Genomics Portal: An Open Platform for Exploring Multidimensional Cancer Genomics Data. Cancer Discovery. May 2012 2; 401).

Example 27

Western Blot Assay

After being subjected to gel electrophoresis, the samples were washed in TBST (0.075% Tween) on shaker and then blocked in 5% Milk for 1 hour. Then 1:2,000 AR Primary (CS: D6F11) in 5% Milk was added and spun overnight at 4° C. The samples were washed three times with TBST for 5 min while shaken. Then 1:2,500 anti-Rabbit HRP Secondary (CS: 7074S) in 5% Milk was added and spun for 1 hour. The samples were washed three times with TBST for 10 min while shaken. ECL Prime was then added using the parafilm method followed by the addition of 1:10,000 anti-GAPDH and 1:15,000 anti-Rabbit HRP.

Example 28

AR transcript level was obtained from RNAseq performed on patient-derived xenograft models of glioblastoma from the Mayo Clinic PDX National Resource. Additional clinical and genomic data from these PDXs are found at ww.mayo.edu/research/labs/translational-neuro-oncology/mayo-clinic-brain-tumor-patient-derived-xenograft-national-resource.

Example 29

T98G cancer cells were implanted into the flanks female C.B-17 SCID mice with or without implanted DHT pellets. Tumor size was measured over time. The results were plotted using Graphpad Prism.

Example 30

GBM Tumor Cell Line Inhibition Assay

AR positive and AR negative GBM cells were plated at clonal density and 1-2 days later were treated with the test compounds at the indicated concentrations. After 10-12 days, the plates were stained with crystal violet. The number of colonies were then counted and normalized to the number of colonies formed in the absence of the test compounds. The results were plotted using Graphpad Prism.

Example 31

AR positive or negative GBM cell lines were treated with seviteronel (2.5-5 uM) for 24 hours prior to treatment with a single fraction of ionizing radiation (0-8 Gy) and then replated at clonal density. After 10-14 days, cells were stained with crystal violet and colonies were counted and normalized to conditions without radiation. Enhancement ratios were calculated by dividing the Dmid (the area under the clonogenic-survival curve) of control conditions by the Dmid of the seviteronel-treated cells.

Example 32

T98G cancer cells were implanted into the flanks of DHT-bearing female C.B-17 SCID mice. After tumors reached approximately 100 mm3 in size, tumors were randomized into control, seviteronel alone (75 mg/kg for 30 days), radiation alone (2 Gy×6 fractions), or combined radiation and seviteronel treatment groups. Tumor size was measured over time and time to tumor doubling was estimated using the Kaplan-Meyer method. The results were plotted using Graphpad Prism.

Results

Glioblastoma Multiforme Exhibits High AR Expression

Figure 2:
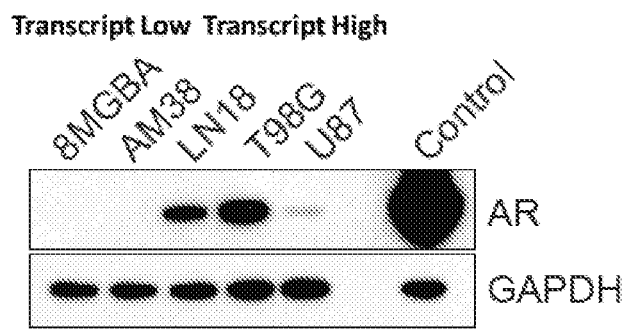
FIG. 2. depicts the AR expression in various glioblastoma multiforme (GBM) tumor cell lines.

Analysis of the Cancer Genome Atlas (TCGA; https://cancergenome.nih.gov/) using the visualization tool, cBioporta (http://www.cbioportal.org/), demonstrated high AR expression levels in several tumor types. In particular, melanoma, lung cancers, colon cancers, renal cancers, breast cancers, gliomas, and glioblastoma multiforme exhibited consistently high levels of AR expression (FIG. 1). Further analysis within the glioblastoma multiforme family indicated that the glioblastoma multiforme cell lines, LN18 and T98G, express substantial levels of the AR, while glioblastoma multiforme cell lines, 8MGBA and AM38, do not (FIG. 2).

Mayo Brain Tumor Patient-Derived Xenografts (PDX) and AR Expression

Figure 3:
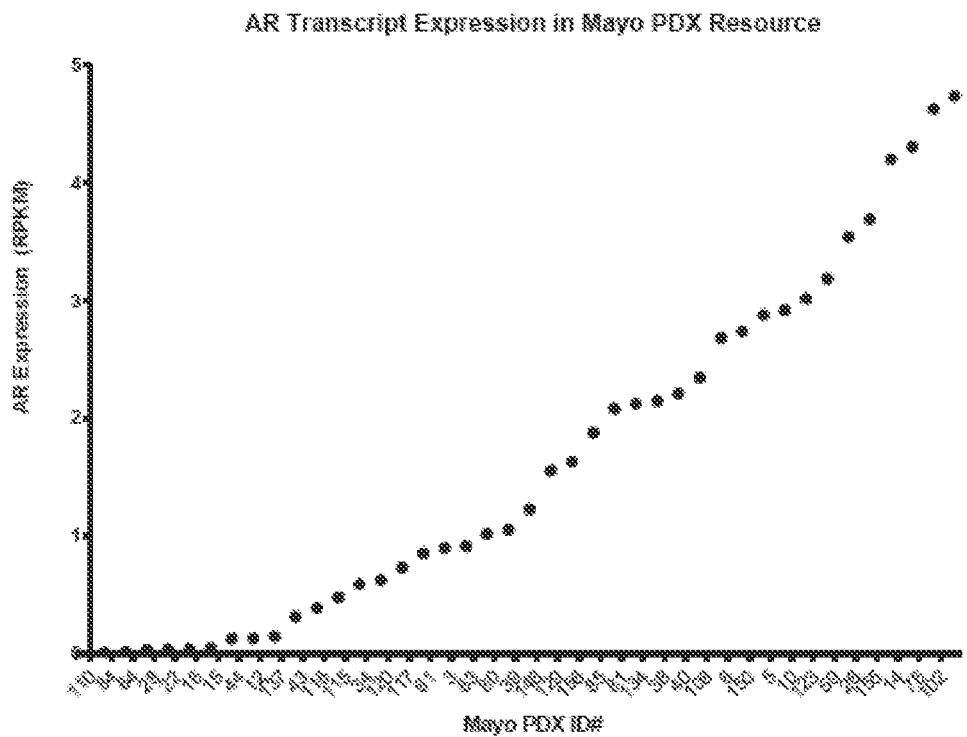
FIG. 3. depicts the AR transcript expression in different Mayo Clinic Brain Tumor Patient-Derived Xenografts.

FIG. 3 shows a comparison of the various PDXs compared to their AR expression obtained from the Mayo Clinic database (FIG. 3).

High AR Expression Cell Line T98G is Sensitive to Androgen Dihydrotestosterone

Figure 4:
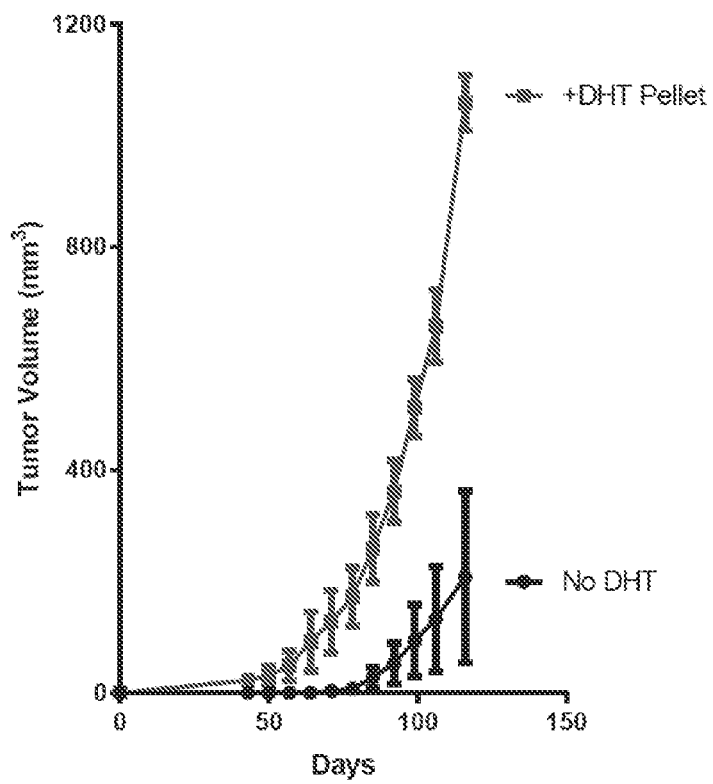
FIG. 4. depicts the relationship between tumor volume over time in the presence of or absence of dihydrotestosterone.

Dihydrotestosterone (DHT) is an androgen, thus, binding to ARs. As such, in the presence of DHT, the tumor volume of the T98G cell line increased more rapidly than when DHT was not present (FIG. 4), establishing that the T98G cell line is sensitive to the presence of androgens.

Seviteronel Inhibits AR Positive GBM Cell Lines

FIGS. 6A, 6B, 6C, and 6D demonstrate that seviteronel (FIG. 5) inhibited the growth of the AR positive glioblastoma multiforme cell lines, LN18 ($G_{50}$=2.7 μM) T98 ($GI_{50}$=4.0 μM), while having little to no effect on the growth of AR negative glioblastoma multiforme cell lines, 8MGBA or AM38.

AR Positive GBM Cell Lines are more Sensitive to Radiation with Seviteronel

FIGS. 7A, 7B, 7C, and 7D demonstrate that LN18 and T98G, which are AR positive cell lines, were more sensitive to radiation therapy in the presence of seviteronel (enhancement ratio of 1.5 and 1.32, respectively) than in the absence of seviteronel. Both 8MGBA and AM38 were similarly sensitive to radiation therapy, however, since they are AR negative cell lines, the presence of seviteronel added little treatment enhancement (enhancement ratio of 1.0 and 1.03, respectively).

Seviteronel and Radiation Therapy Exhibit A Synergistic Effect On Tumor Growth

Figure 8:
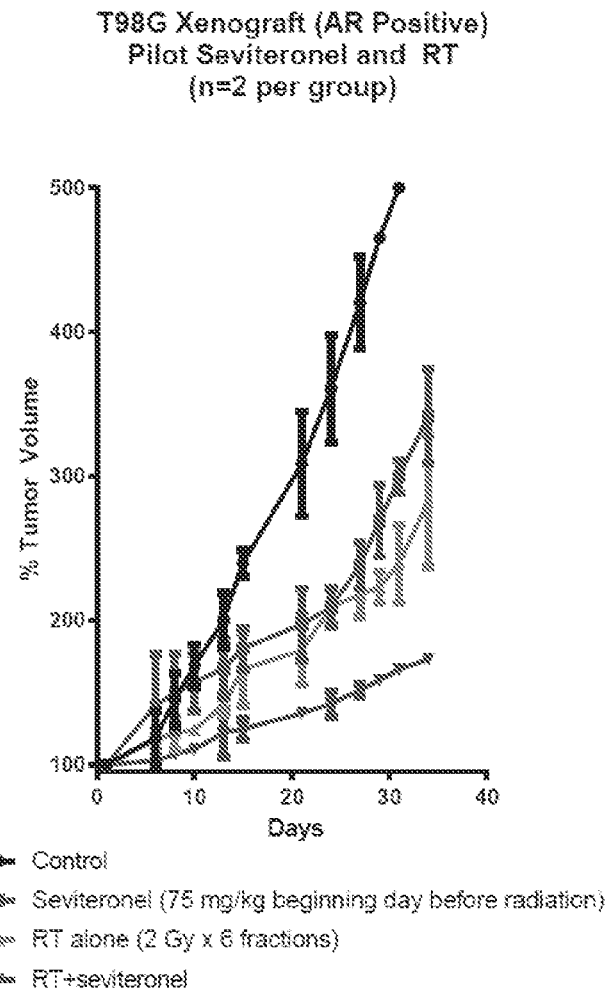
FIG. 8 depicts the tumor volume in a mouse T98G xenograft model over 35 days with no treatment, seviteronel and radiation therapy alone, and the method of treatment combining seviteronel and radiation therapy, wherein seviteronel was administered on days 1-30 and radiation therapy was carried out on days 2-7.

FIG. 8 depicts the relation between tumor volume over 35 days in a mouse T98G xenograft model and demonstrates the synergistic effect of treatment with radiation therapy and seviteronel on reducing increases in tumor volume. Without any treatment, the tumor volume increased by approximately 5 fold. With seviteronel or radiation therapy alone, the tumor volume increased approximately 2-3 fold. When employing the treatment with radiation therapy and seviteronel, the tumor increased by only approximately 50%.

Seviteronel and Radiation Therapy Inhibit Tumor Growth From Doubling

Figure 9:
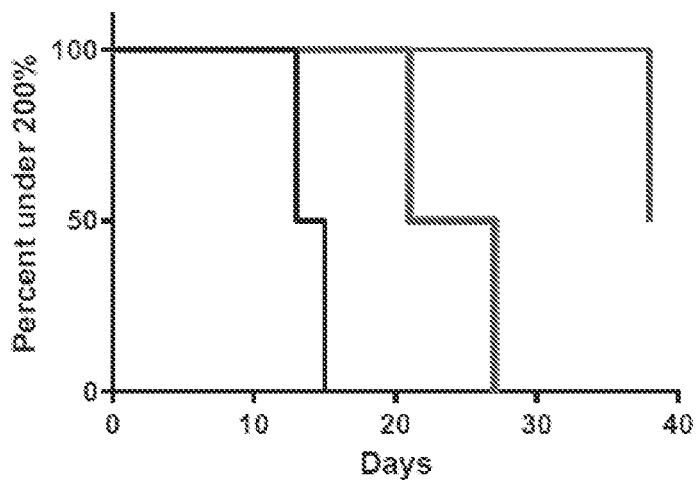
FIG. 9 depicts the relationship between number of days of treatment compared to the percent of mice with tumors that has less than doubled (has increased by less than 200%).

FIG. 9 demonstrates that treatment with radiation therapy and seviteronel resulted in a marked inhibition of tumor growth. Within 15 days, the tumors in 100% of the untreated mice had doubled in tumor volume. Both sets of mice treated with either seviteronel or radiation therapy alone had a tumor twice the size compared to the start within 30 days. In contrast, none of the mice treated with seviteronel and radiation therapy experienced a doubling in tumor volume after 30 days, thus, demonstrating the synergistic effect of the treatment with seviteronel and radiation therapy versus either therapy alone.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method of treating a subject suffering from a brain tumor, wherein the brain tumor is a glioma, meningioma, or medulloblastoma, the method comprising the administration of radiation therapy and an effective amount of a pharmaceutical composition comprising: (1) seviteronel, or a pharmaceutically acceptable salt thereof, (2) dexamethasone, or a pharmaceutically acceptable salt thereof; and (3) a pharmaceutically acceptable carrier.

2. The method of claim 1, wherein the amount of seviteronel in the composition is:
   (a) in a range of about 150 mg-750 mg;
   (b) in a range of about 400 mg-650 mg;
   (c) 600 mg; or
   (d) 450 mg.

3. The method of claim 1, wherein the amount of dexamethasone in the composition is:
   (a) in a range of about 0.25 mg-1000 mg;
   (b) in a range of about 0.40 mg-0.60 mg; or
   (c) 0.5 mg.

4. The method of claim 1, wherein:
   (a) the amount of seviteronel in the composition is in a range of about 150 mg-750 mg, and the amount of dexamethasone in the composition is in a range of about 0.25 mg-1000 mg;
   (b) the amount of seviteronel in the composition is in a range of about 150 mg-750 mg, and the amount of dexamethasone in the composition is in a range of about 0.40 mg-0.60 mg;
   (c) the amount of seviteronel in the composition is in a range of about 150 mg-750 mg, and the amount of dexamethasone in the composition is 0.5 mg;
   (d) the amount of seviteronel in the composition is in a range of about 400 mg-650 mg, and the amount of dexamethasone in the composition is in a range of about 0.25 mg-1000 mg;
   (e) the amount of seviteronel in the composition is in a range of about 400 mg-650 mg, and the amount of dexamethasone in the composition is in a range of about 0.40 mg-0.60 mg;
   (f) the amount of seviteronel in the composition is in a range of about 400 mg-650 mg, and the amount of dexamethasone in the composition is 0.5 mg;
   (g) the amount of seviteronel in the composition is 600 mg, and the amount of dexamethasone in the composition is in a range of about 0.25 mg-1000 mg;
   (h) the amount of seviteronel in the composition is 600 mg, and the amount of dexamethasone in the composition is in a range of about 0.40 mg-0.60 mg;
   (i) the amount of seviteronel in the composition is 600 mg, and the amount of dexamethasone in the composition is 0.5 mg;
   (j) the amount of seviteronel in the composition is 450 mg, and the amount of dexamethasone in the composition is in a range of about 0.25 mg-1000 mg;
   (k) the amount of seviteronel in the composition is 450 mg, and the amount of dexamethasone in the composition is in a range of about 0.40 mg-0.60 mg; or
   (l) the amount of seviteronel in the composition is 450 mg, and the amount of dexamethasone in the composition is 0.5 mg.

5. The method of claim 1, wherein the brain tumor is a glioblastoma.

6. A method of treating a subject suffering from a brain tumor, wherein the brain tumor is a glioma, meningioma, or medulloblastoma, the method comprising the administration of radiation therapy to a subject having been administered an effective amount of a pharmaceutical composition comprising: (1) seviteronel, or a pharmaceutically acceptable salt thereof, (2) dexamethasone, or a pharmaceutically acceptable salt thereof, and (3) a pharmaceutically acceptable carrier.

7. The method of claim 6, wherein the amount of seviteronel in the composition is:
   (a) in a range of about 150 mg-750 mg;
   (b) in a range of about 400 mg-650 mg;
   (c) 600 mg; or
   (d) 450 mg.

8. The method of claim 6, wherein the amount of dexamethasone in the composition is:
   (a) in a range of about 0.25 mg-1000 mg;
   (b) in a range of about 0.40 mg-0.60 mg;
   (c) 0.5 mg.

9. The method of claim 6, wherein:
   (a) the amount of seviteronel in the composition is in a range of about 150 mg-750 mg, and the amount of dexamethasone in the composition is in a range of about 0.25 mg-1000 mg;
   (b) the amount of seviteronel in the composition is in a range of about 150 mg-750 mg, and the amount of dexamethasone in the composition is in a range of about 0.40 mg-0.60 mg;
   (c) the amount of seviteronel in the composition is in a range of about 150 mg-750 mg, and the amount of dexamethasone in the composition is 0.5 mg;
   (d) the amount of seviteronel in the composition is in a range of about 400 mg-650 mg, and the amount of dexamethasone in the composition is in a range of about 0.25 mg-1000 mg;
   (e) the amount of seviteronel in the composition is in a range of about 400 mg-650 mg, and the amount of dexamethasone in the composition is in a range of about 0.40 mg-0.60 mg;
   (f) the amount of seviteronel in the composition is in a range of about 400 mg-650 mg, and the amount of dexamethasone in the composition is 0.5 mg;
   (g) the amount of seviteronel in the composition is 600 mg, and the amount of dexamethasone in the composition is in a range of about 0.25 mg-1000 mg;
   (h) the amount of seviteronel in the composition is 600 mg, and the amount of dexamethasone in the composition is in a range of about 0.40 mg-0.60 mg;
   (i) the amount of seviteronel in the composition is 600 mg, and the amount of dexamethasone in the composition is 0.5 mg;
   (j) the amount of seviteronel in the composition is 450 mg, and the amount of dexamethasone in the composition is in a range of about 0.25 mg-1000 mg;
   (k) the amount of seviteronel in the composition is 450 mg, and the amount of dexamethasone in the composition is in a range of about 0.40 mg-0.60 mg; or
   (l) the amount of seviteronel in the composition is 450 mg, and the amount of dexamethasone in the composition is 0.5 mg.

10. The method of claim 6, wherein the brain tumor is a blioblastoma.

11. A method of treating a subject suffering from a brain tumor, wherein the brain tumor is a glioma, meningioma, or medulloblastoma, the method comprising the administration of radiation therapy to a subject having been administered an effective amount of: (1) seviteronel, or a pharmaceutically acceptable salt thereof, and (2) dexamethasone, or a pharmaceutically acceptable salt thereof.

12. The method of claim 11, wherein the amount of seviteronel is:
    (a) in a range of about 150 mg-750 mg;
    (b) in a range of about 400 mg-650 mg;
    (c) 600 mg; or
    (d) 450 mg.

13. The method of claim 11, wherein the amount of dexamethasone is:
    (a) in a range of about 0.25 mg-1000 mg;
    (b) in a range of about 0.40 mg-0.60 mg; or
    (c) 0.5 mg.

14. The method of claim 11, wherein:
    (a) the amount of seviteronel is in a range of about 150 mg-750 mg, and the amount of dexamethasone is in a range of about 0.25 mg-1000 mg;
    (b) the amount of seviteronel is in a range of about 150 mg-750 mg, and the amount of dexamethasone is in a range of about 0.40 mg-0.60 mg;
    (c) the amount of seviteronel is in a range of about 150 mg-750 mg, and the amount of dexamethasone is 0.5 mg;
    (d) the amount of seviteronel is in a range of about 400 mg-650 mg, and the amount of dexamethasone is in a range of about 0.25 mg-1000 mg;
    (e) the amount of seviteronel is in a range of about 400 mg-650 mg, and the amount of dexamethasone is in a range of about 0.40 mg-0.60 mg;
    (f) the amount of seviteronel is in a range of about 400 mg-650 mg, and the amount of dexamethasone is 0.5 mg;
    (g) the amount of seviteronel is 600 mg, and the amount of dexamethasone is in a range of about 0.25 mg-1000 mg;
    (h) the amount of seviteronel is 600 mg, and the amount of dexamethasone is in a range of about 0.40 mg-0.60 mg;
    (i) the amount of seviteronel is 600 mg, and the amount of dexamethasone is 0.5 mg;
    (j) the amount of seviteronel is 450 mg, and the amount of dexamethasone is in a range of about 0.25 mg-1000 mg;
    (k) the amount of seviteronel is 450 mg, and the amount of dexamethasone is in a range of about 0.40 mg-0.60 mg; or
    (l) the amount of seviteronel is 450 mg, and the amount of dexamethasone is 0.5 mg.

15. The method of claim 11, wherein the brain tumor is a glioblastoma.

16. A method of treating a subject suffering from a braintumor, wherein the brain tumor is a glioma, meningioma, or medulloblastoma, the method comprising the administration of radiation therapy and an effective amount of: (1) seviteronel, or a pharmaceutically acceptable salt thereof, and (2) dexamethasone, or a pharmaceutically acceptable salt thereof.

17. The method of claim 16, wherein the amount of seviteronel is:
    (a) in a range of about 150 mg-750 mg;
    (b) in a range of about 400 mg-650 mg;
    (c) 600 mg; or
    (d) 450 mg.

18. The method of claim 16, wherein the amount of dexamethasone is:
    (a) in a range of about 0.25 mg-1000 mg;
    (b) in a range of about 0.40 mg-0.60 mg;
    (c) 0.5 mg.

19. The method of claim 16, wherein:
    (a) the amount of seviteronel is in a range of about 150 mg-750 mg, and the amount of dexamethasone is in a range of about 0.25 mg-1000 mg;
    (b) the amount of seviteronel is in a range of about 150 mg-750 mg, and the amount of dexamethasone is in a range of about 0.40 mg-0.60 mg;
    (c) the amount of seviteronel is in a range of about 150 mg-750 mg, and the amount of dexamethasone is 0.5 mg;
    (d) the amount of seviteronel is in a range of about 400 mg-650 mg, and the amount of dexamethasone is in a range of about 0.25 mg-1000 mg;
    (e) the amount of seviteronel is in a range of about 400 mg-650 mg, and the amount of dexamethasone is in a range of about 0.40 mg-0.60 mg;
    (f) the amount of seviteronel is in a range of about 400 mg-650 mg, and the amount of dexamethasone is 0.5 mg;
    (g) the amount of seviteronel is 600 mg, and the amount of dexamethasone is in a range of about 0.25 mg-1000 mg;
    (h) the amount of seviteronel is 600 mg, and the amount of dexamethasone is in a range of about 0.40 mg-0.60 mg;
    (i) the amount of seviteronel is 600 mg, and the amount of dexamethasone is 0.5 mg;
    (j) the amount of seviteronel is 450 mg, and the amount of dexamethasone is in a range of about 0.25 mg-1000 mg;
    (k) the amount of seviteronel is 450 mg, and the amount of dexamethasone is in a range of about 0.40 mg-0.60 mg; or
    (l) the amount of seviteronel is 450 mg, and the amount of dexamethasone is 0.5 mg.

20. The method of claim 16, wherein the brain tumor is a glioblastoma.

* * * * *